United States Patent [19]
Goldowsky

[11] Patent Number: 5,924,975
[45] Date of Patent: Jul. 20, 1999

[54] LINEAR PUMP

[75] Inventor: Michael P. Goldowsky, Valhalla, N.Y.

[73] Assignee: International Business Machines Corporation, Armonk, N.Y.

[21] Appl. No.: 08/686,618

[22] Filed: Jul. 19, 1996

Related U.S. Application Data

[60] Provisional application No. 60/003,043, Aug. 30, 1995.

[51] Int. Cl.$^6$ ...................................................... A61M 1/10
[52] U.S. Cl. .............................................................. 600/16
[58] Field of Search ........................................ 600/16, 17

[56] References Cited

U.S. PATENT DOCUMENTS

| | | | |
|---|---|---|---|
| 2,249,843 | 7/1941 | Marsland | 384/292 |
| 2,515,110 | 7/1950 | Bornstein | 230/55 |
| 3,669,517 | 6/1972 | Hughes | 384/115 |
| 3,726,574 | 4/1973 | Tuffias et al. | 384/133 |
| 3,923,060 | 12/1975 | Ellinwood, Jr. | 128/260 |
| 3,964,805 | 6/1976 | Schulien | 384/399 |
| 4,210,409 | 7/1980 | Child | 417/241 |
| 4,272,226 | 6/1981 | Osborne | 417/418 |
| 4,375,941 | 3/1983 | Child | 600/16 |
| 4,389,849 | 6/1983 | Gasser et al. | 62/6 |
| 4,427,308 | 1/1984 | Sandberg | 384/115 |
| 4,437,815 | 3/1984 | McMullen | 417/418 |
| 4,675,563 | 6/1987 | Goldowsky | 310/15 |
| 4,692,673 | 9/1987 | DeLong | 417/417 |
| 4,799,421 | 1/1989 | Bremer et al. | 92/162 R |
| 4,824,337 | 4/1989 | Lindner et al. | 417/417 |
| 4,883,367 | 11/1989 | Maruyama | 384/114 |
| 4,908,012 | 3/1990 | Moise et al. | 600/16 |
| 4,965,864 | 10/1990 | Roth et al. | 318/135 |
| 5,049,134 | 9/1991 | Golding et al. | 604/151 |
| 5,147,281 | 9/1992 | Thornton et al. | 600/16 |
| 5,360,445 | 11/1994 | Goldowsky | 623/3 |
| 5,370,463 | 12/1994 | Asada et al. | 384/115 X |
| 5,676,162 | 10/1997 | Larson, Jr. et al. | 128/899 |
| 5,676,651 | 10/1997 | Larson, Jr. et al. | 604/33 |
| 5,693,091 | 12/1997 | Larson, Jr. et al. | 612/3 |
| 5,702,430 | 12/1997 | Larson, Jr. et al. | 607/1 |

FOREIGN PATENT DOCUMENTS 2084408  9/1980  United Kingdom .

OTHER PUBLICATIONS

Stolfi et al, "A Magnetically Suspended Linearly Driven Cryogenic Refrigerator," NASA Report N84–15345, Dec. 1, 1983, pp. 263–303.

U.S. Patent application Serial No. 08/684,115, filed Jul. 19, 1996.

*Machine Design*, "Innovative Motor Lets Low–Cost Simulators Rock and Roll," Sep. 1994, p. 26.

*Primary Examiner*—William E. Kamm
*Attorney, Agent, or Firm*—Francis L. Conte

[57] ABSTRACT

A linear pump includes a housing having a bore and axially spaced apart inlet and outlet. A first check valve is joined to the housing for controlling flow of fluid through the bore. A piston is disposed coaxially in the housing bore for axial translation therein and includes a piston bore and axially spaced apart inlet and outlet. A second check valve is joined to the piston for controlling fluid flow through the piston bore. A linear motor includes a plurality of axially adjoining drive coils disposed in the housing, and a pair of axially spaced apart magnet rings disposed in the piston and spaced radially inwardly of the drive coils for magnetically cooperating therewith to axially oscillate the piston in the housing for cyclically pumping the fluid in turn through the housing and piston inlets and outlets in unidirectional flow through the housing and piston bores.

62 Claims, 16 Drawing Sheets

2 LEAFLETS

SINGLE DISK

LINEAR PUMP

The present invention claims the priority date of provisional application Ser. No. 60/003,043, filed on 30 Aug. 1995 and now abandoned, incorporated herein by reference.

BACKGROUND OF THE INVENTION

The present invention relates generally to fluid pumps, and, more specifically, to a pump configured for pumping blood in a living body.

Although significant progress has been made over the last two decades to develop implantable left ventricular assist devices and artificial hearts, two significant problems still remain. These problems are long-term hemocompatibility and mechanical reliability.

The hemocompatibility problem is universally due to the use of polymeric or rubber pumping ventricles that are prone to eventual thrombogenesis, clotting, calcification, etc. They are not yet suitable for reliable, long-term pumping. In addition, flex life is a concern. With regard to mechanical robustness and reliability, it has taken decades of improvement to attain a relatively low level of reliability compared to what is needed. This mechanical problem is due to the fact that all approaches are too complex. They involve many moving parts, they use ball bearings and other bearings prone to wear, fatigue, and shock, incorporated are springs, linkages, etc. Whatever the basic approach, they have all been prone to wear and friction. Some use mechanical pusher plates and some hydraulically actuated rubber ventricles.

Low mechanical reliability of the Total Artificial Heart (TAH) is supported by the "cause of termination" in Table 1, which compares the life records of four leading total artificial heart programs. The table is taken from the recently published NHLBI document entitled, "Report of the Workshop on the Artificial Heart." The table is found on Page 36 of the workshop in a paper written by well-known William S. Pierce, M.D., Professor of Surgery, Hershey Medical Center, entitled, "Overview of Mechanical Circulatory Support Program."

As can be seen, implanted pumps have lasted up to 160 days, and in all three long term cases, the cause of termination was mechanical failure.

At the end of his paper, Dr. Pierce states that further research and development is required in the areas of long-term reliability and in the development of better polymeric materials. This applies to left ventricular assist devices as well. The following recommendations are excerpted from his paper.

"Recommendations

The concept of a totally implantable TAH is a reality. A continuing commitment of the Federal Government is requested to materialize this concept into human application. No foreseeable major technical barrier exists to reach toward this goal. The tasks, however, are enormous, which are to be accomplished in each step and every area of development. Future advancement in the general area of science and technology would certainly contribute to this endeavor. However, further research and development in the following areas would facilitate the development of a TAH in particular and will benefit researchers included in MCSS development and long-term implantable medical devices:

1. Engineering improvements in reliability and longevity.
2. Better understanding of circulatory physiology of TAH recipients.
3. Development of new synthetic polymeric materials."

Poor electromechanical reliability of the drive mechanism and long term hemo-reliability of the blood contacting surfaces remain as the two "main" problems in developing heart assist devices suitable for long term (years) human use.

Blood contacting surfaces for decades have been made of flexible polymer ventricles which cause thrombosis, calcification, and clotting due to chemical incompatibility with blood. Some recent novel continuous flow devices like the Jarvik 2,000 propeller or centrifugal pumps may be made of titanium or solid pyrolytic carbon to get around the biocompatibility problem. These devices however, possess shaft seal problems, ball bearing problems running in blood, poor efficiency, thrombosis, and physiological control problems. Hence, even these new approaches do not satisfy all of the requirements needed for a long term reliable pump.

It is an object of this invention to solve virtually all known blood pumping problems and to meet all of the requirements of an assist device by eliminating polymeric materials, by minimizing blood shear stresses to eliminate blood damage and hemolysis, by eliminating all mechanical contact and wear, by minimizing the formation of thromboemboli, by utilizing pyrolytic carbon or a future hemo-compatible coating on rigid blood contacting surfaces, by providing high efficiency, by providing integral means to measure blood pressure which may be used to control the device, by providing an effective means to dissipate motor heat into the blood, by providing a small enough device for optimal implantation in the chest with minimal conduit lengths, and by providing flexibility in the design to allow withdrawing blood from different areas of the heart. These and other advantages are met by the instant design.

SUMMARY OF THE INVENTION

A linear pump includes a housing having a bore and axially spaced apart inlet and outlet. A first check valve is joined to the housing for controlling flow of fluid through the bore. A piston is disposed coaxially in the housing bore for axial translation therein and includes a piston bore and axially spaced apart inlet and outlet. A second check valve is joined to the piston for controlling fluid flow through the piston bore. A linear motor includes a plurality of axially adjoining drive coils disposed in the housing, and a pair of axially spaced apart magnet rings disposed in the piston and spaced radially inwardly of the drive coils for magnetically cooperating therewith to axially oscillate the piston in the housing for cyclically pumping the fluid in turn through the housing and piston inlets and outlets in unidirectional flow through the housing and piston bores.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DESCRIPTION OF THE PREFERRED EMBODIMENT(S)

The problems presented above are solvable now, using a design that is capable of employing the best blood compatible surface throughout the pump (pyrolytic carbon), in conjunction with an all-rigid titanium pump; having only one moving part, a noncontacting linear motor actuator, that has already demonstrated five years of continuous operation with 100% reliability in a previous application. The concept to be presented has the potential of far exceeding the goal of a five-year life with 90% reliability. This can be achieved now using existing materials.

The long-term blood compatibility problem has been solved by eliminating the problem. No polymeric materials are used. The pump will not wear out and can be used again for other recipients. Thus, the potential exists for large cost savings and greater affordability. Two satisfactory, off-the-shelf heart valves are employed. They are easily replaced as better designs become available in the future; whether for improved efficiency, better hemodynamic reliability, or lower noise. The invention is not static, it is capable of incorporating future improvements.

The following nomenclature is used herein:

EXPLANATION OF NOMENCLATURE $\tau$=Time duration of one LVAD pump cycle (sec).

This equals piston eject time+reset time.

$\tau_s$=Piston eject time (sec)

This is commonly referred to as pump systole time.

$\tau_d$=Piston reset time (sec).

This is sometimes referred to as pump "diastole" time and must not be confused with diastole of the natural heart.

s=Subscript denoting systole (eject) portion of cycle.

d=Subscript denoting diastole (reset) portion of cycle.

Q=Q Flowrate, in general.

$Q_s$=Systole flowrate, ejected from pump.

$Q_d$=Diastole (reset) flowrate, through piston bore, internal to pump.

$Q_n$=Net pump flowrate, valve leakages considered.

η=Efficiency.

μ=Blood absolute viscosity.

B=Magnetic field flux density, in general.

L/m=Liters per minute.

ΔP=Pressure drop.

OTHER: Technical sections include a Legend for defining other symbols and units as appropriate.

Figure 1:
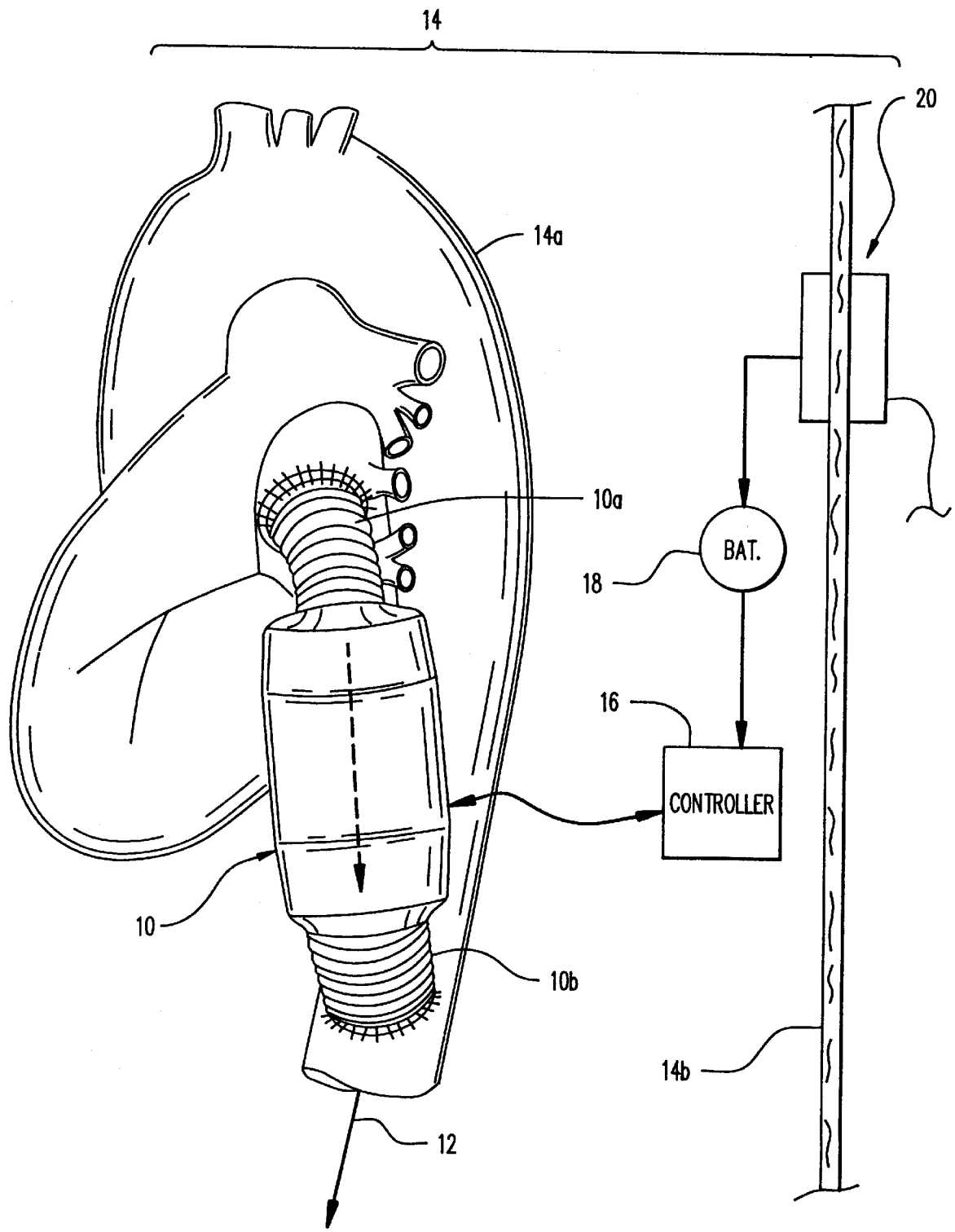
FIG. 1 is a schematic representation of the linear pump joined to a human heart inside a chest for assisting in pumping blood through the body in an exemplary configuration.

Illustrated in FIG. 1 is a linear pump 10 configured in accordance with an exemplary embodiment for being implanted into a living body for pumping fluid or blood 12. In the exemplary embodiment illustrated, the pump 10 is configured as a left ventricular assist device (LVAD) surgically attached between the left atrium and descending aorta of a human heart 14a. The pump 10 includes a suitable inlet tube 10a sutured to an opening in the left atrium, and a suitable outlet tube 10b sutured to the descending aorta.

The pump 10 is controlled by an electrical controller 16 suitably electrically joined thereto, and is powered by an implanted battery 18 electrically joined to the controller 16. The pump 10 and cooperating controller 16 and battery 18 are implanted in the body 14 below the skin 14b. The battery 18 is periodically charged by a conventional induction charging device 20 which includes an induction coil inside the body 14 and a cooperating external induction coil outside the body in a known configuration.

Figure 2:
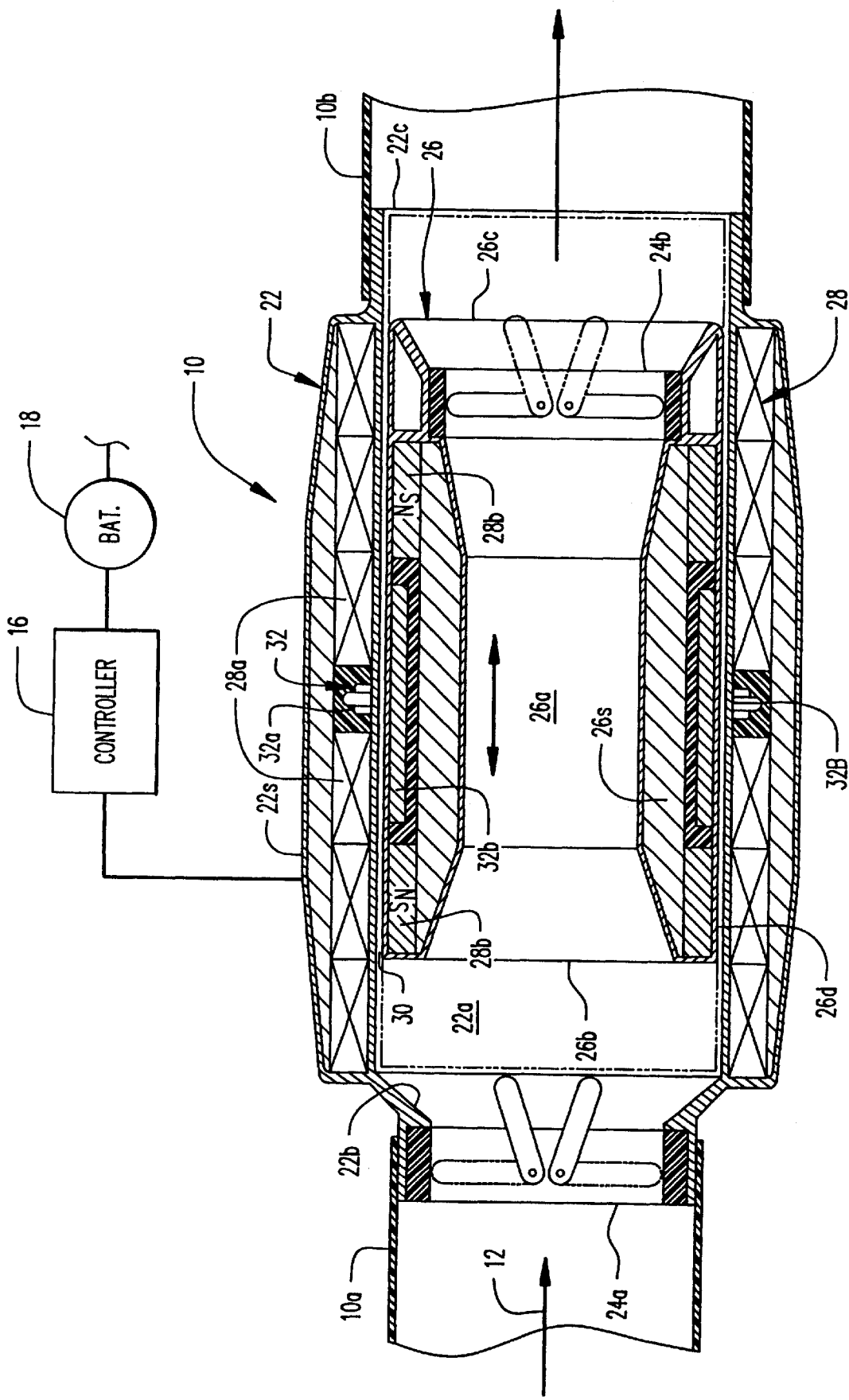
FIG. 2 is an axial, partly sectional view of the linear pump illustrated in FIG. 1 in accordance with an exemplary embodiment including a piston mounted inside a housing and axially reciprocated by a linear motor formed integrally therewith for unidirectionally pumping blood using a pair of check valves.

FIG. 2 illustrates an exemplary embodiment of the pump 10 which includes a hollow housing 22 having a coaxial, smooth cylindrical center bore 22a disposed in flow communication between a pump or housing inlet 22b and a pump or housing outlet 22c axially spaced apart from each other at opposite ends of the housing 22. A first, one-way or, check valve 24a is suitably fixedly joined in the housing inlet 22b for controlling flow of the blood 12 through the housing bore 22a. In an alternate embodiment, the first valve 24a may instead be located in the housing outlet 22c.

A cylindrical, hollow piston 26 is disposed coaxially in the housing bore 22a for axial translation therein. The piston 26 includes a coaxial, smooth center bore 26a disposed in flow communication between a piston inlet 26b and a piston outlet 26c axially spaced apart from each other at opposite ends of the piston 26. A conventional second, one-way or, check valve 24b is suitably fixedly joined in the piston outlet 26c for controlling flow of the blood 12 through the piston bore 26a. In an alternate embodiment, the second valve 24b may instead be installed in the piston inlet 26b.

A linear motor 28 includes a plurality of axially adjoining, coaxial stator drive coils 28a disposed in the housing 22, which cooperate with a pair of axially spaced apart permanent magnet rings 28b disposed in the piston 26. The magnet rings 28b are also spaced radially inwardly of the drive coils 28a for magnetically cooperating therewith to axially translate or oscillate the piston 26 in the housing 22 for cyclically pumping the blood 12 in turn through the housing and piston inlets 22b, 26b and outlets 22c, 26c in unidirectional flow through the housing and piston bores 22a, 26a.

Since the pump 10 is specifically configured in this exemplary embodiment for pumping blood 12 in a living body, the housing 22 and piston 26 are preferably encapsulated in a suitable biocompatible material for being implanted into the body and pumping blood through the housing and piston bores 22a, 26a. In the preferred embodiment illustrated in FIG. 2, this is accomplished by forming the outer surfaces of the housing 22 and piston 26 in the form of suitably thin Titanium shells or cans, which themselves may be suitably coated with a biocompatible material such as carbon if desired.

The piston 26 illustrated in FIG. 2 includes a cylindrical outer surface or journal 26d which is predeterminedly spaced radially inwardly of the housing bore 22a to define a hydrodynamic bearing therewith having a radial gap 30 for receiving a portion of the blood 12 from the housing bore 22a as bearing fluid for hydrodynamically supporting the oscillatory piston 26 in the housing 22. The housing inner surface defining the housing bore 22a is suitably smooth, and the complementary piston journal 26d is also in most part smooth. The piston gap 30 is nominally a circular annulus which extends completely between the opposite end of the piston 26 in flow communication with the housing bore 22a.

In operation, the linear motor 28 is powered for magnetically axially translating the piston 26 in the housing bore 22a in a forward or eject stroke followed in turn by an aft or reset stroke. The piston 26 is therefore axially reciprocated forward and aft to linearly pump the blood 12 in a unidirectional forward flow from the housing inlet 22b to the housing outlet 22c. The one-way check valves 24a,b cooperate with the reciprocating piston 26 for obtaining the unidirectional flow. In FIG. 2, the piston 26 is illustrated in solid line in the middle of its forward eject stroke with the first valve 24a being open and the second valve 24b attached to the piston 26 being closed for blocking reverse flow through the piston bore 26a. In this way, the piston 26 provides a forward moving plug which pushes the blood 12 forwardly and outwardly through the housing outlet 22c. At the same instant, the blood 12 enters the housing inlet 22b.

In the aft reset stroke, the piston 26 moves rearwardly which causes the second valve 24b to open as shown in phantom line, with the first valve 24a being closed as also shown in phantom line. The closed first valve 24a restrains reverse blood flow, while the open second valve 24b allows the piston 26 to reset without flow obstruction to the beginning of its travel for the next cycle. In this way, the linear pump 10 is effective for pumping the blood 12 in periodic pulses in only the forward direction.

The piston 26 is entirely bathed in the blood 12 and provides pumping action through its bore 26a. And, the flow of the blood 12 in the piston gap 30 effects a hydrodynamic bearing for suspending the piston 26 away from the housing bore 22a for providing substantially frictionless movement thereof.

Hydrodynamic bearing forces may be developed solely by the axial movement of the piston 26 in the housing 22, or the piston may be rotated for circumferentially developing hydrodynamic pressure in the bearing fluid, with the bearing defining a journal bearing. In this embodiment, suitable means are provided for spinning the piston 26 for effecting journal bearing performance as described in more detail hereinbelow.

The linear pump 10 is the ultimate in mechanical simplicity, as it has only one moving part. This part is the linearly oscillating hollow-piston 26 that pumps blood unidirectionally through the pump. The pump uses the moving valve 24b in the piston 26 and the stationary valve 24a in the housing inlet 22b to accomplish this pumping action, which will be explained in more detail in the following sections.

The piston moves back and forth inside the smoothly polished bore 22a of titanium which is the pump's housing. These surfaces are Biolite coated (Biolite is a tradename of Carbomedics Corporation for their carbon coating) and are polished to the same high degree used in heart valves. The housing contains stationary electrical coils 28a that are energized to produce an axial force on the piston. The piston is the moving part of the motor. It contains two magnet rings 28b that are hermetically sealed therein. The LVAD pump 10 is 1.80" in diameter and 3.10" long in one embodiment.

Two groups of three drive coils 28a, whose function is to produce axial motion, are shown. They are round and surround the cylindrical bore 22a of the pump. These coils are hermetically sealed in a corrosion-resistant titanium alloy can whose entire blood-contacting surface is coated with Biolite. (Biolite is a tradename of Carbomedics Corporation for their carbon coating.) Biolite is used to coat the titanium stiffener rings used in prosthetic heart valves because of its long-term hemocompatibility and nonthrombogenicity. The piston 26, which is the moving part of the motor or armature, has two integral magnet rings 28b, one at each end. Since the magnets are the moving element, there are no flexing leads to break, unlike other linear motor designs. The entire piston (magnets, etc.) is encapsulated in an hermetically sealed can of titanium which too is coated with Biolite on all blood-contacting surfaces. The piston 26 fits in the bore 22a with a radial clearance of 0.0015 in, or 37 microns. Since the pump is entirely filled with blood, blood is also in this gap 30. The piston is multifunctional in that it is also its own self-supporting 360° hydrodynamic bearing. By rotating the piston in the bore at only 72 RPM using the same linear motor, the piston becomes a well proven journal bearing which operates in all orientations.

The piston stays very well centered in the bore as it rotates and oscillates. Thus, there is no contact with the housing, no wear, and negligible friction. The stiffness of the bearing is 3,300 lb/in or equal to that of a ball bearing suspension. It handles the motor's magnetic side loads with high margin. This motor design is one of proven, inherently low side loads and is ideally suited for this application. Bearing rotation is accomplished with the same motor using an innovative separate winding in accordance with a preferred embodiment describe hereinbelow. Two very thin, 0.010 in thick coils are energized with constant current. They are located at each end of the stator. Two coils require no extra space than one so redundancy is provided using two. The motor produces constant torque without the need for commutation circuitry or rotary position sensors, unlike brushless DC motors. The only electronics needed is to supply a low constant current to the winding. This feature allows the bearing load capacity to be independent of blood viscosity.

In the journal bearing design section, it is shown why the application of a constant torque gives this bearing a very unique and desirable characteristic. Namely, it self-compensates for any viscosity changes of the blood. In other words, bearing load capacity using a constant torque input, remains unchanged. It is invariant with viscosity. If the blood viscosity decreases, for example from medication use, or if hematocrit levels reduce due to illness, the bearing's 72 RPM increases on its own, which restores the original load capacity. Conversely, the bearing automatically slows down if viscosity should increase for any reason. Thus, this bearing will work equally well in recipients of different blood types whose absolute viscosity might conceivably be different for Asians, South Americans, Indians, etc. This, and other important advantages such as the bearings ability to absorb tremendous shock loads, are discussed in Sections F and G.

Now, how does the oscillating piston pump blood? A standard 25 mm aortic heart valve 24b (any can be used) is mounted in the right side of the moving piston, which is hollow. In FIG. 2, the piston is shown in the center of its stroke, moving to the right, pushing against systolic pressure. Motor energy conversion efficiency by the way, is 85%, against 120 mm Hg of systolic pressure. This valve 24b is forced closed so the piston pushes blood through the pump's outlet to the descending aorta. The piston moves from left to right, a total stroke distance of 0.9 inches in 55 msec, which is called the systolic time. As the piston moves to the right, the stationary mitral valve 24a on the left side is open, allowing blood to enter the pump. This valve is relatively large (27 mm) to possess low-pressure drops. This allows the pump to be filled by left-atrial pressure, assuming the left atrium is used as the pump's inlet. A negative pressure or suction behind the piston is avoided (as it would cause red blood cell rupture) by using a large enough inlet valve.

When the piston reaches near the end of its stroke, it is decelerated by the motor 28, stopped, and reversed in direction. As it reverses direction, the moving valve is forced to open. The introduction of some back flow and systolic pressure down the bore of the piston closes the inlet valve 24a. This valve eliminates the backflow of blood as the piston resets. The piston goes back to its starting position nearly effortlessly, as aortic pressure exists on both sides, and little power is consumed. Reset time is denoted as diastolic time, and varies from 0.33 sec to 0.10 sec, as pump frequency increases to obtain flow rates of 3 to 10 L/min. Systolic time is arbitrarily held constant at 55 msec for low to medium flow rates, and is decreased to 50 msec at or above 8 L/min to increase motor efficiency. A similar physiologic response occurs in the natural heart.

A miniature position sensor 32 shown is located between the two groups of three drive coils 28a. It is used to switch on and off each individual coil in sequence, as the piston moves. This unique use of switchable coils in a voice coil linear motor allows one to put current in only those coils that are instantaneously positioned over the moving magnet. In this way, current is not used in nonforce-producing coils, resulting in an efficiency increase of 33%. This commutation technique makes it possible for a voice coil motor to have a large stroke compared to the magnet ring's axial length, in this case, 3 to 1. A long stroke reduces the required piston diameter. This not only reduces imposed systolic force but increases piston speed, both of which raise motor efficiency. These factors have enabled an outstanding motor energy conversion efficiency of 85% to be realized. Motor coil commutation is discussed in Section C.

The pump size was dramatically reduced over conventional 70 to 85 ml rubber ventricle designs by using a small stroke volume of 18.8 ml. This is typically ¼ the stroke volume of an adult's heart. Thus, the pump runs at typically four times the frequency of the natural heart. For larger patients, it would be run at a slightly higher frequency and for smaller recipients it would be run slower. A smaller pump than that shown in FIG. 2 would be used for children or where an output of 10 L/m was not required.

Even though the pump's beat rate is higher than physiologic, the pump's peak (systolic) flow rate was kept considerably less than that of the natural heart to promote a conservative physiologic design. Continuous flow pumps apparently are physiologically acceptable. This design is somewhere in between the large pulsatile flow of the natural heart and continuous flow.

As more flowrate is demanded of the pump, its frequency is merely increased. Its stroke length remains constant at 0.9" to maximize motor efficiency. Systolic pressure is accurately determined from the motor drive current. Since motor force varies linearly with current for this type of motor, differential pressure across the piston is directly proportional to monitored current, and because the piston is frictionless, the piston acts like an ideal pressure transducer. Systolic pressure readings are independent of ambient air pressure changes. The unique use of the motor 28 as a pressure transducer for physiological control is discussed in Section J. Pump physiological control can be based on a variety of control options. For example, if the patient's EKG signal is reliable and if the right heart is in good condition, pump frequency can be made to track the beat rate of the natural heart. Future potential also exists for using right atrium Blood-Oxygen Saturation Level to control cardiac output. LVAD control options are discussed in Section J. Pump output as a final example automatically tracks the activity level or cardiac demand of the recipient using an adaptive physiological control based on systolic pressure.

The continuous and instantaneous position of the piston is obtained by using two redundant, miniature magneto resistors 32a as described in more detail hereinbelow. They sense grooves machined into the diameter of an iron sleeve 32b located beneath the titanium can of the piston. By counting pulses, the piston position is determined. An end-point sensor resets the pulse count to zero at the end of the stroke. The proposed design does not require any additional space, as the space between magnet rings 28b is unused and the space between drive coil phases exists. These sensors produce a 3 volt output pulse directly with minimal electronics. They are solid state and do not age. They possess a 10 KHZ frequency response for excellent control system performance. Piston velocity is directly obtainable by determining time between pulses. Use of two sensors displaced ¼ pitch apart produces velocity direction information. Redundancy is easily obtainable. This is discussed in Section D. These sensors are now used in hard disk drive flying heads by IBM, and are the utmost in reliability and small size.

Voice coil motors in general are easily controlled due to their inherent linear response, due to invariance of the force constant. Acceleration and deceleration routines are easy to execute, with a good position signal. Acceleration and deceleration power loss is only 1% due to the low mass of the piston. Any type of flowrate waveform can be programmed for systole. However, a constant velocity profile maximizes motor efficiency. So, to simplify the pump efficiency analysis, a constant velocity profile was used in each direction. A plot of this profile is presented in FIG. 34.

The small size of the proposed pump, 1.80 in diameter× 3.10 in long (only 129 ml volume) will allow the pump to be implanted in the chest cavity adjacent the heart 14a between the left atrium and the descending aorta, using short conduit lengths for connection. This minimization of artificial conduits is a cited advantage because long-term hemodynamic reliability at the inlet and outlet is also required, not just in the pump. FIG. 1 shows the suggested implantation location of the LVAD. It is proposed to withdraw blood from the left atrium as shown and expel it into the descending aorta. The descending aorta is in close proximity and leaves sufficient space for pump insertion. Thoracic cavity measurements have already been made (during open-heart surgery) to support this location.

Other locations, such as removing blood from the left ventricular apex, can be considered if advantageous. The physiological pumping characteristics of the pump are easily modified by the proper choice of inlet valve size to meet physiological pressure drop requirements of the location chosen (discussed in Section B). The stationary valve 24a can also be put at the pump outlet 22c instead of at the inlet. Then, physiological pressure drop constraints are eliminated. Additional versatility is gained by the method chosen for physiological control (discussed in Section J).

Going back to the design of the linear motor illustrated in FIG. 2, two magnetic flux shells or rings 22s, 26s are found in the housing and piston. The rings 22s,26s are high-saturation magnetic iron alloyed with 3% Vanadium and 45% cobalt. Called Vanadium Permendure, it is used to save weight. It enables thinner flux shells to be employed than attainable with normally used silicon iron. Vanadium permendure can be used up to 23,000 gauss, but is conservatively used in this design between 16,000–21,000 gauss. The radial flux from the right magnet ring 28b passes through the force-producing coil 28a and into the stationary outer shell 22s. It travels axially down the permendure shell 22s, passes through the left force-producing coil 28a, and enters the left magnet ring 28b. This magnet ring is magnetized radially opposite from the right. The flux then passes into the inner shell 26s of the hollow piston 26, where it travels back to the right magnet ring to complete the closed magnetic circuit. The flux is constant in the piston's center shell or core 26s, so no eddy currents or hysteresis loss can be produced here. However, as the magnet oscillates back and forth relative to the outer shell or core 22s, some eddy currents and hysteresis losses are generated within it, but are shown to be negligible at the maximum pump frequency of 10 HZ. Furthermore, the eddy currents generated in the coil can are shown to be minuscule due to the high resistivity of the titanium alloy and its small thickness, 0.010 in.

With regard to the dissipation of the motor waste heat, the motor is so efficient (84–85% from 3 to 10 L/min), that there is very little heat to dissipate in the blood. At 10.2 L/min flow rate, the power to be dissipated is a maximum at only 2.6 W. At a typical flow of 5.4 L/min, it is only 0.56 W. The heat transfer section shows that the oscillating motion of the piston, which causes bidirectional fluid flow to occur in the gap 30, creates extremely favorable conditions which allow transfer of this heat right through the gap. The blood motion creates a large convective heat transfer coefficient at both the coil-can ID, and the piston can OD. This transfers the heat flow directly into the piston 26 where it is easily transferred into the blood, flowing at high velocity through its bore 26a. The temperature rise of the blood in the gap 30 is calculated to be only 1.3° F., and the coil-can surface temperature in contact with the blood will only rise 2.7° F. above body temperature. The above results conservatively assume all of the heat generated passes through the gap, and the pump OD loses no heat. Of course, some of the heat in the coil will also travel axially to its ends where it is disposed of directly into the main flow of blood, as the piston covers and uncovers end portions of the coils 28a during the cycle. No problems are anticipated with dissipating the heat of the motor.

Figure 30:
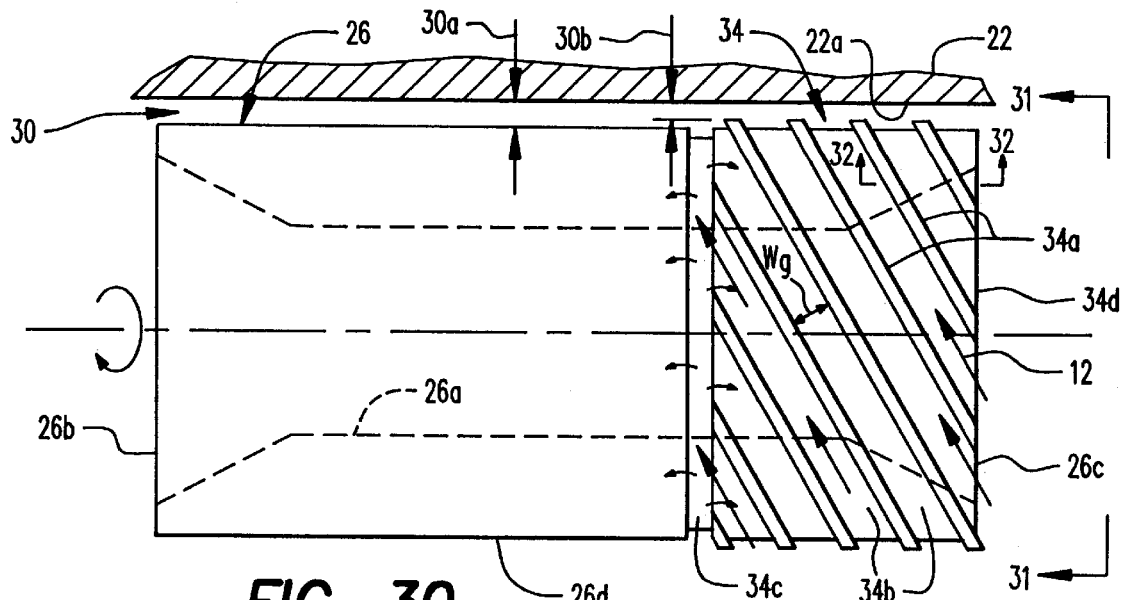
FIG. 30 is a plan view of the piston illustrated in FIG. 2 including an integral screw pump at one end for providing make-up fluid flow into the bearing gap for accommodating end leakage therefrom.
Figure 31:
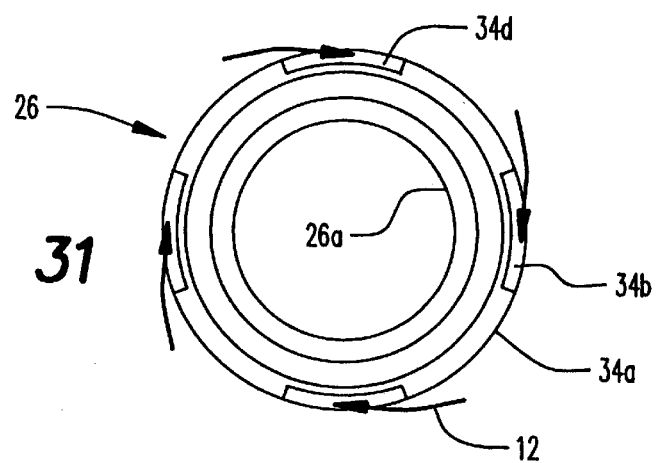
FIG. 31 is a radial end view of the screw pump illustrated in FIG. 30 taken along line 31—31.
Figure 32:
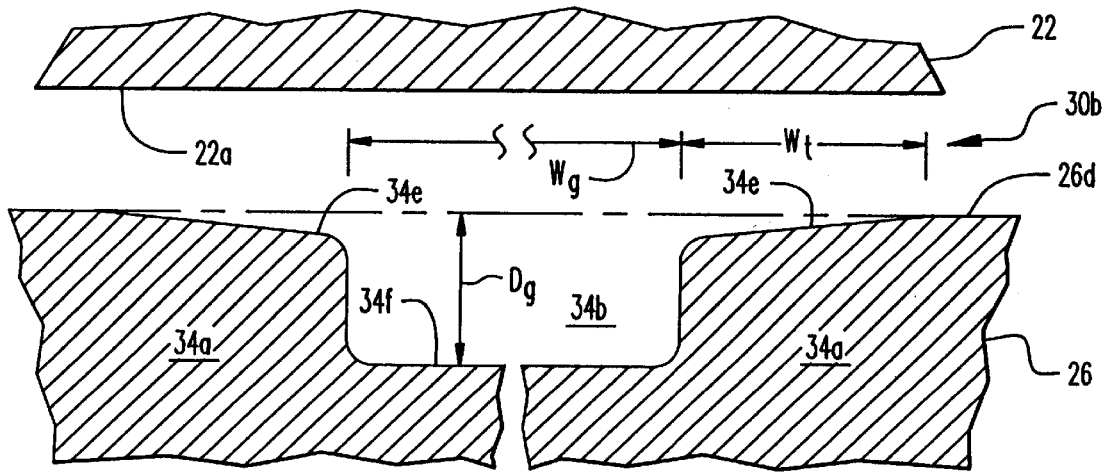
FIG. 32 is a sectional view through an exemplary one of the screw threads and grooves illustrated in FIGS. 30 and taken along line 32—32.

The heat dissipation mechanism leads us to another interesting feature provided in the design of the journal bearing. Journal bearings develop their load capacity by generating an internal pressure due to the rotation. In this design, the pressure rise is only 0.5 PSI, or 26 mm Hg. This pressure creates fluid leakage out the ends of the bearing and one must replenish this for the bearing to operate. This is why one's automobile engine requires an oil pump, to resupply the journal bearings. In this innovative design, no external pump is needed. It has been substituted with a very simple and previously proven type of screw viscosity pump. The screw pump 34 is illustrated in FIGS. 30–32 in accordance with a preferred embodiment and includes a 0.005 in deep screw thread cut into the end surface of the piston. It is located at the right end of the piston 26 surrounding the valve 24b. The flow induced by this miniature pump is forced down the length of the thread by piston rotation relative to the stationary housing. The design of this screw viscosity "pump" is straightforward, is noncontacting, uses the same radial gap as the rest of the bearing, and requires no additional axial space. It is 8 mm long and fits in the axial space required for the systole valve. Thus, we have a self-contained journal bearing with its own integral pump.

The screw pump 34 serves yet another important function as well. It pumps a continuous flow of fresh new blood through the piston gap 30 to carry away what little heat did not pass directly into the piston. This is one of the factors that causes the temperature rise of this blood to be so low and allows the coil-can surface to stay so cool. This extremely cool running makes for very reliable motor coils with virtually no chance of degradation. The use of rectangular instead of round wire also enhances heat conduction out of the coil, resulting in a further reduction in coil temperature rise.

A final function of the screw pump 34, and by no means the least important, is to wash out the piston gap with fresh blood, which it does every 3.0 sec. Some washout of the bearing also occurs during systole from systolic pressure, but this by itself is insufficient. The pump insures a short residence time of blood in the bearing. Hence, the shear stress induced in the blood by bearing rotation, although low, does not act for a long enough duration on the blood cells to damage even blood platelets, which are less robust than red cells. This is discussed in detail in Section H.

This leads us, finally, to a few comments about bearing hemocompatibility and why it will function reliably for long-term use. The oscillating motion of the piston 26 creates a back-and-forth low shearing stress on the blood in the gap, which is hydrodynamically precisely calculatable due to the simple geometry involved. Also, flow is shown to be highly laminar in the gap, so no turbulence exists. Hence, the only blood damage possible is that due to any excessive shear stresses that have sufficiently long duration. Cell damage dependency on shear stress magnitude and duration has been experimentally established and is presented in graphical form in NIH publication No. 85-2185, revised September 1985, entitled "Guidelines for Blood-Material Interactions, Report of the NHLBI Working Group." The specifications given in this document for the elimination of shear-dependent damage in the bearing have been met by a wide margin. Also, other subjective and established good design practices such as continuous washout have been instituted. Extremely low hemolysis results obtained using a similar clearance seal in a rigid-vane artificial heart (Section H) can only lead to the conclusion that the proposed journal bearing will not damage blood. This, and other calculations and comparisons with higher blood shear in conventional pumps, is discussed in detail in Section H.

For a journal bearing to operate without contact its end leakage must be made up with externally supplied flow. To do this, the screw viscosity pump 34 is used at one end of the piston 26. It provides pressurized flow to the bearing which also unidirectionally washes out the gap 30 with fresh blood. This enables the bearing to be long term hemocompatible. The constant washout of the bearing gap 30 will eliminate or minimize the formation of thromboemboli in the bearing.

An alternate piston support would use a linear hydrodynamic blood bearing, similar to the oil bearing disclosed in U.S. Pat. No. 5,360,445 entitled "Blood Pump Actuator".

Figure 27:
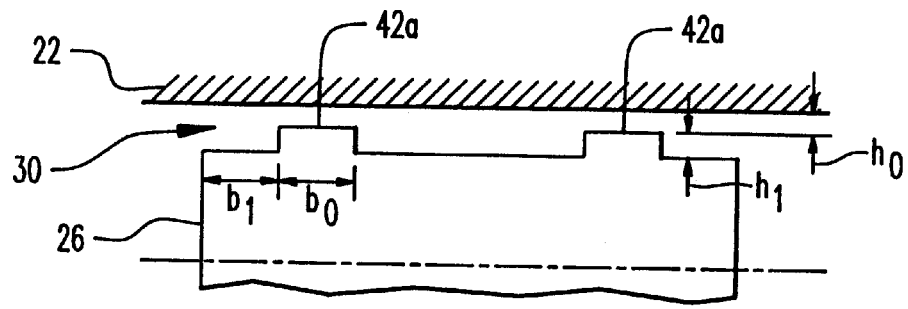
FIG. 27 is a schematic representation of a double acting axial hydrodynamic bearing formed within the gap between the piston and housing of the linear pump illustrated in FIG. 2 for supporting the piston therein in accordance with an exemplary embodiment.
Figure 28:
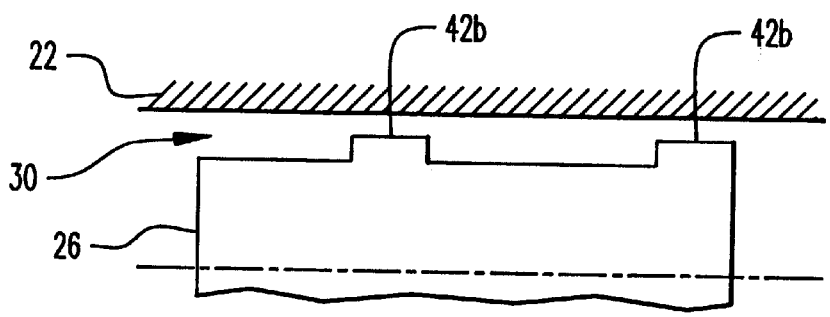
FIG. 28 is a schematic representation of a single acting axial hydrodynamic bearing formed within the gap between the piston and housing of the linear pump illustrated in FIG. 2 for supporting the piston therein in accordance with an exemplary embodiment.

This bearing can be made to work in blood with proper choice of parameters. Two configurations are shown in FIGS. 27 and 28. A disadvantage of this linear bearing is that its load capacity for a given axial velocity is a function of blood viscosity so it must be over designed using minimum expected blood viscosity. This results in inherent tradeoffs for stiffness and blood shear. Advantages are that it does not require a pressurizing pump or rotation.

A magnetic suspension could also be used to support the piston but this is too complex and less reliable.

The piston 26, since it is near frictionless, is ideally suitable for use as a differential blood pressure transducer. Motor current is directly proportional to this pressure. Pump control algorithms based on pressure have been used in the past. Pump frequency is merely speeded up to increase flowrate as needed. This is all independent of environmental pressure changes.

Since the internal volume of the pump remains fixed no venting or compliance chamber is needed. Thus, the motor and piston can be hermetically sealed in hemocompatible titanium for long term reliability.

The control system is based on position and velocity feedback loops. Piston position is obtained using the non-contacting position sensor 32. The magneto resistor sensor 32 senses right through the titanium cans and is integratable without requiring additional axial space.

The basic linear blood pump 10 includes a non-contacting non-wearing rigid hollow piston 26 immersed in a blood filled stationary rigid housing 22; the piston 26 having a clearance seal gap 30 with the housing; the piston 26 linearly oscillates with respect to the housing 22 using linear actuator means 28, and valve means 24a,b provided in the housing 22 and piston 26 to provide unidirectional flow of blood through the piston and pump.

Potential Use

1. Using the device 10 for pumping blood during open heart surgery. It would replace roller pumps that currently damage blood. The device would be practical since the piston is removable from the housing outlet 22c and all parts cleanable and sterilizable. This is a potentially very large market. Miniature electronics and implantation constraints do not exist which would drastically shorten time to market.

2. Various Heart assist devices are used as transplant bridges for patients, such as the Novacor and Heartmate LVADs.

3. The self contained journal bearing may find many additional uses from disc drive spindles to cars, lawn mowers engines, and electric motors.

4. The motor commutation method can be used for linear motors as well as some rotary motors to improve efficiency and to reduce cogging.

5. Kidney dialysis machines, heart/lung machines for open-heart surgery.

In summary, the following advantages and desirable features are listed for the proposed LVAD pump design:

1. Biocompatible Biolite carbon surfaces are used throughout the pump. This material is the best nonthrombogenic material available and is proven for long-term use in heart valves. Its use will provide the best long-term reliability over any other choice of material for the foreseeable future.

2. Simplicity of design is achieved with one moving part, the piston 26; that is noncontacting, nonwearing, and is basically of unlimited life.

3. The LVAD pump 10 is highly efficient and small enough in size to allow ideal implantation in the chest cavity adjacent the heart. No compliance chamber or venting is required, and it is hermetically sealed.

4. The viscosity-compensating hydrodynamic journal bearing is extremely stiff and stable. The piston gap 30 is an ideal transfer surface of heat into the main blood supply. The temperature rise of the blood and its contacting surfaces is minuscule.

5. The extremely low hemolysis for the bearing (which will be proven by a worse case calculation in Section H) is accomplished by making this a primary constraint in its design. Low blood shear in the gap is insured by using acceptable piston velocities and as large a gap as practical. With ejection and reset times of only a fraction of a second's duration, the threshold value for blood-cell damage is not approached.

6. The piston 26, in conjunction with the motor 28 is the LVAD's own systolic pressure transducer which may be used to physiologically control the LVAD. There is no need for extraneous pressure sensors which increases complexity and have their own reliability concerns.

7. Constant washout of the bearing gap to eliminate long term thrombus generation.

8. Although listed last, but no less important, is the incorporation of a trouble-free linear motor type of proven design and almost of the same size, which has already demonstrated a five-year continuous use, reliability of 100%, which includes its control electronics.

Figure 3:
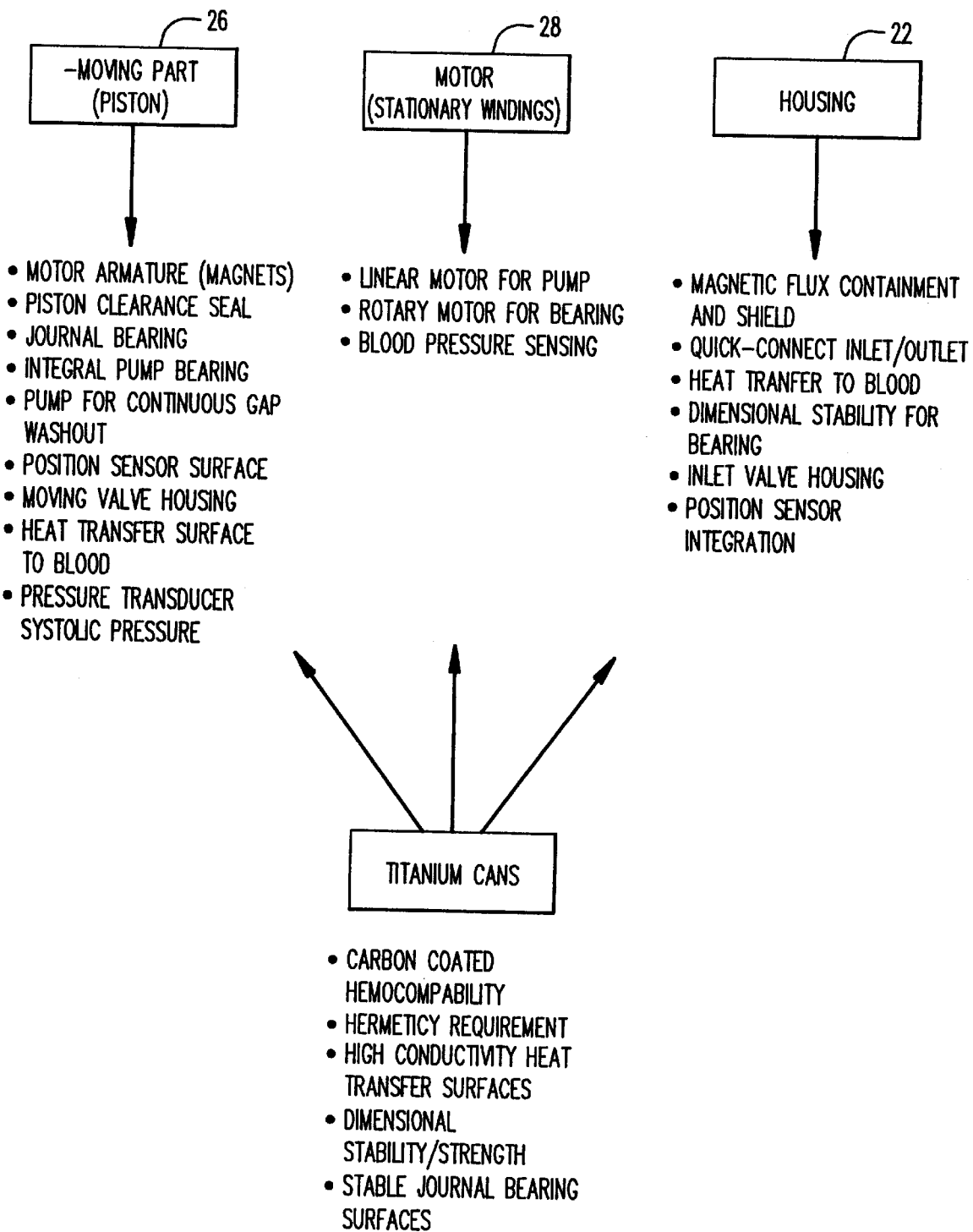
FIG. 3 is a flow chart representation of the major parts of the linear motor illustrated in FIG. 2.
Figure 4:
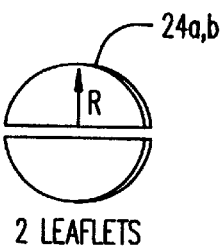
FIGS. 4 and 5 are schematic representations of an exemplary bileaflet check valve which may be used in the pump illustrated in FIG. 2.
Figure 5:
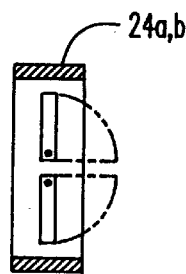
Figure 6:
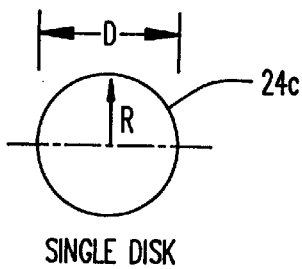
FIGS. 6 and 7 are schematic representations of a single disc check valve which may be used in the pump illustrated in FIG. 2 in an alternate embodiment.
Figure 7:
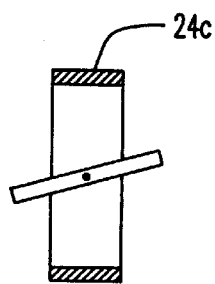

The main goal of the linear pump design approach is long-term reliability. This is best achieved by examining the history of other programs, thereby permitting a common sense choice which is elegant in its simplicity. Reliability is simplicity and simplicity is elegance. The pump 10 achieves its simplicity through the synergistic (multifunctional use) of each and every component. This is summarized in FIG. 3, where the four primary mechanical components of the pump are shown in boxes. The multifunctional uses of the component are listed below each. The titanium encapsulating cans are a common component that is synergistic with the other tree.

Section A—Valve Selection

1. Mechanical Bileaflet

Importance of Low Leakage and the Double Leaf Design

The closing volume $V_3$ or backflow of blood as the valve closes, is an important parameter to minimize as it is the main contributor in reducing the pump's volumetric efficiency (in addition to steady state leakage when closed). The gross stroke volume of the pump 10 is 18.8 ml which is ¼ that of the natural heart. So a back leakage of say 1 ml produces a cycle leakage of 5%. Since two valves 24a,b are used in the pump, the total closing leakage is the sum of both or approximately 10%. Although acceptable, this leakage substantially reduces overall system efficiency. Closing volume leakage is referred to as volume $V_3$ in the industry and is published for each valve size. The bigger the valve, the larger $V_3$. For large valves, $V_3$ is more than closed steady state leakage and for smaller valves, both leakages are about the same.

A two leaf valve like that made by Carbomedics Corp. and others, leaks about half as much as a single disc valve of the same size. Why is this so? A simple and fairly accurate model of closing leakage states that $V_3$ is equal to the swept volume of the disc or leaflets which assumes no slippage of flow past the leaf. As shown in the FIGS. 4–7, the swept volume of two half size leafs of the valves 24a,b is half that of a single disc of the same open area or diameter. The conclusion, therefore, is that a bileaflet valve is about twice as efficient on closing volume.

Steady State Leakage—Since steady state leakage when closed is proportional to the total disc perimeter:

$$\text{Leakage ratio} = \frac{\text{Bileaflet perimeter } \pi D + D}{\text{single disc perimeter } \pi D} = \frac{\pi + 1}{\pi} = 1.32$$

The bileaflet valves 24a,b have 32% more leakage when closed. But this is not a large penalty provided steady state leakage over the cycle is less than or about the same as closing volume. This is generally true in this application as will be seen in the valve performance table.

The Carbomedics Valve—Double leaf valves are now favored for use over a single disc. They are available from Carbomedics Corp., Duromedics and Saint Jude. Carbomedics makes standard size valves ranging from 17 mm and up in 2 mm increments. Their valves can be used with little if any modification in the proposed design. They are chosen for the pump 10 because of:

1. Proven long life in accelerated testing. Life testing is routinely done for Q.C. purposes under accelerated conditions of 12–16 HZ for 600 million cycles. There is no significant wear or degradation in performance at 1 billion cycles and beyond. The projected life in the LVAD at typically 5 cycles/sec (5 L/m) is 27 years. There is little question as to the valve's 5 year reliability even at higher average rates of flow.

2. Low closing volume $V_3$.

3. Very thin housing ring allows a bigger valve I.D. for less pressure drop.

4. Low steady state leakage. Leafs and housings are computer matched from a large inventory for optimal fits and results in low leakage when closed.

5. Easy to mount in the pump using biocompatible thermoset epoxy DGEBPA which is used in implantable devices such as pacemakers and vascular access devices. One or two-thousands inch clearance with the pump housing is suggested by Carbomedics to insure not squeezing the valve and allowing the adhesive to bond. Press fitting in place is a less desirable option.

6. Noise level lower than almost all other mechanical valves (0.98 sones). (Ref. "An In-Vitro Study of Mechanical Heart Valve Sound Loudness", by Erickson et al, Journal of Heart Valve Disease, 1994, pp. 330–334.)

7. Cavitation threshold and damage superior to Duromedics valve and equal to St. Jude. (Ref. "Cavitation Threshold Ranking and Erosion Characteristics of Bileaflet Heart Valve Prostheses", by G. Richard et al., Journal of Heart Valve Disease, 1994, pp 94–101.)

2. Tissue Valve Option and Future Upgrade Ability

Any type valve can be used in the pump. Mechanical valves were chosen because of their clinically proven long-term life and ease of mounting in the pump. Tissue valves, although very quiet, last 4–15 years in humans. In the pump 10 running at 4 Hz, life is not known but is projected to be less than the 5 years required. Tissue valves also require more space in the pump. When one valve is open, the other is closed. So pump operation at 4 Hz (for one valve) results in an equivalent 8 Hz frequency. This higher frequency might be attenuated by body tissue and a more continuous perception of sound or humming may result. As valve technology advances and tissue type valves are improved, the best available valves can then be implemented for near silent operation. Present tissue valves almost meet the life requirement now. In the near future, polymeric valves or better tissue valves will become available. There is no reason they could not be incorporated in the pump. As lower leakage mechanical valves also become available, they can be retrofitted into existing pumps to further improve efficiency. Present overall system efficiency is excellent at 65%, but a small improvement in valve leakage would increase this to 70%.

3. Physiological Constraints and Sizing of Inlet Valve a. Ejection Requirements (Pump Systole)

During Ejection—(Pumping part of the cycle). In the design of the pump 10, during ejection, the stationary valve 24a is open. The ejection flow rate is large due to the desirable high velocity of the piston for maximizing motor efficiency. A sufficiently large valve is needed here which has a low pressure drop in order not to create a substantial negative pressure (or suction) behind the piston. This would cause red cell rupture. Consequently, the valve pressure drop permitted is limited to available pressure at the pump inlet. The pump inlet 22b is the left atrium whose pressure is a function of cardiac output and blood volume. Left atrial pressure during heart failure may run between 15 and 25 mmHg. A valve pressure drop of only 5–6 mm Hg was conservatively used at 10 L/m which resulted in selecting a 27 mm valve (when using an ejection time of 0.050 sec). This valve is a standard catalogue item. The choice of valve size obviously depends upon the time chosen for systole Ts (eject time) as this determines the peak piston velocity and hence peak systole flow rate. This small 6 mm drop allows the pressure behind the piston to remain positive. This large valve has higher closing volume leakage. The pump volumetric efficiency calculations which follow, are based on valve leakage data supplied by Carbomedics Corp.

Valve leakage can be compensated for by using a larger stroke volume for the pump, for example 23.4 cc instead of 18.8. Increasing stroke volume decreases valve leakage as a percent of cycle volume thereby increasing volumetric efficiency. This was done in the second pump design to be presented which is 49.5 mm in diameter. Inlet valve pressure drop increases to 9 mm Hg which is still acceptable, so a second pump design with a larger stroke volume is presented which flattens overall system efficiency at high flow rates. Pump outside diameter increased 3.8 mm which is one of the trade offs that need be considered in a final design.

The point to be made is this: the valves chosen and motor design parameters used, which give excellent performances, are illustrative only, and may not constitute an optimum design. The pump 10 has a great deal of flexibility in choosing design parameters so that optimal physiological performance can be achieved. Increasing pump housing diameter from its existing 45.5 mm to 49.3 mm for example, allowed the use of a larger piston bore with much lower reset (or diastole) flow resistance. This improves system efficiency at high rates of flow.

Decreasing $T_s$ at only the highest flow rates 8–10 L/m only affects motor efficiency at these flow rates and does not change volumetric efficiency. This is yet another option to minimize bore pressure drop without increasing pump O.D.

b. Piston Reset Requirements

Piston Reset (Pump diastole). During reset, the moving valve 24b opens as the stationary valve 24a closes. The reset speed is generally less than ejection speed, so flow rate through the piston is low. This allows the use of a smaller (25 mm) aortic valve. The ΔP generated across this valve is also across the piston and is a maximum of 15 mm Hg @ 10 L/m for the reset time chosen of 0.05/sec at 10 L/m. There is no restriction on permitted ΔP for this valve other than pump efficiency. The larger the ΔP, the more reset work the motor has to do which decreases system efficiency. The reset motor force is typically 0.6 lbs at 10 L/m whereas ejection force is 3.0 lbs. Thus, the 15 mm pressure drop accounts for 20% of the work done in the cycle at 10 L/m. Use of a larger valve increases leakage faster than ΔP decreases so a 25 mm valve is probably close to optimum.

The flow rate pressure drop characteristic of different size inlet and moving valves is easily modeled computing the discharge coefficient for each size from published flow rate data. The overall system efficiency versus flow rate can then be modeled using a conventional computer program.

System efficiency can then be peaked at any desired flow rate or it can be held relatively flat as was done, by choice of valve size, ejection time, reset time, stroke and most importantly piston diameter. Choice of piston diameter also has a major impact on the magnetic circuit design; that enough cross section of material exists in the piston for the return of flux. With this constraint satisfied, the remaining room left is allotted to the bore I.D., and space for the moving valve which constrains its maximum diameter. One can see that all of these design variables interact. It is most noteworthy that such an efficient design could be realized that satisfies all of the physiological, magnetic and hydrodynamic constraints for the bearing.

4. Outlet Valve Option and Applicability to Right Assist Device

The exemplary pump design presented uses an inlet valve 24a. One can eliminate this valve 24a and its associated small pressure drop by using a stationary valve at the pump outlet instead (not shown). The only slight disadvantage seen in doing so at this time is the small additional pressure drop of the valve to be overcome during ejection. A few mm Hg penalty is not large but a significant physiological advantage results: Minimal pressure is required to fill the pump from the pump inlet reservoir.

If the LVAD is used as a Right Heart Assist pump and is used to pull blood from the right atrium, one would like as low an inlet pressure drop as possible. This is because venous return pressure to the right atrium may at times be only 5–10 mm Hg so no valve at the pump inlet is an ideal situation. Venous return pressure is then sufficient to fill the pump under positive pressure.

This positive pressure constraint used for pump filling is conservative. Ventricular filling pressures in the natural heart may at times be negative (between 3 and 5 mm Hg) and blood cell hemolysis or rupture does not occur. This additional margin should be added to the safety margin already designed into the inlet valve by its size selection (27 mm).

Section B—Linear Motor Design

1. Magnetic Circuit and Force Generation

Referring back to FIG. 2, the linear motor 28 accounts for nearly all of the pump's structure. The moving element, i.e.

the piston 26, includes the two magnet rings 28a attached to the central iron shell or yoke 26s which is hollow. This inner yoke serves to return the magnetic flux between magnet rings. The outer magnetic ring 22s serves to direct magnet flux between the drive coils 28a.

Figure 8:
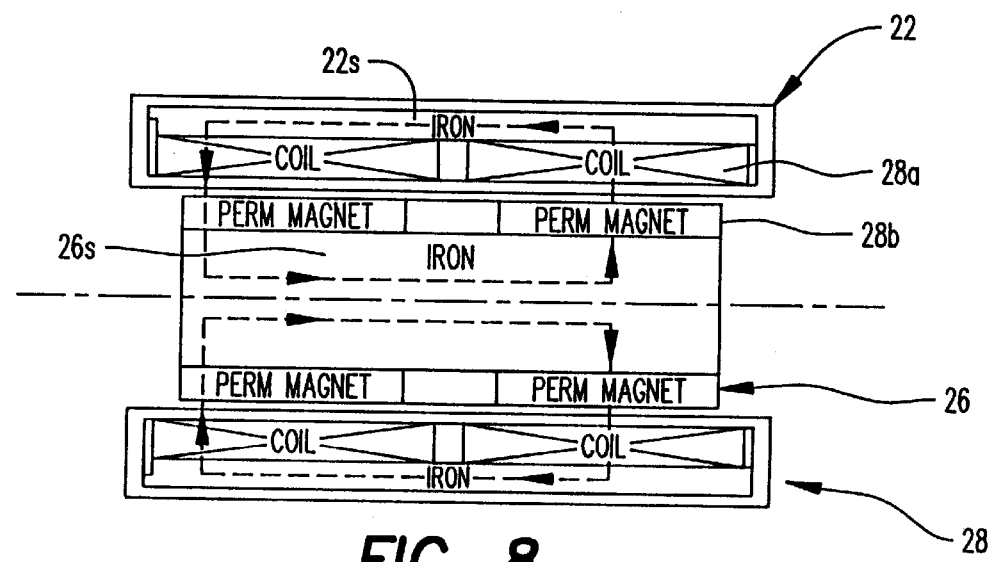
FIG. 8 is a schematic representation of an exemplary linear motor and the magnetic flux path therethrough.

This closed flux path is clearly shown in FIG. 8 which is a schematic of the motor 28. The radial magnet flux passes from the outward magnetized right magnet ring 28b, radially up through the right side drive coils 28a and into the outer magnetic shell 26s. The flux passes axially down the shell and radially back into the oppositely magnetized magnet ring 28b on the left side. From here it travels back into the center iron core 26s to complete the magnetic circuit. Electromagnetic force generated on the piston 26 is due to the interaction of the tangential coil current with the radial magnetic flux that passes through the coil. This force, which is known as the Lorentz force, is equal to B (the magnetic flux density)×I (the current in the winding)×L (the length of wire perpendicular to the magnetic field). Since the magnetic field only exists over the axial length of the magnet, only those coil turns that are directly in the magnetic field produce force. The current direction in the right set of three coils 28a is directed oppositely from the three coils 28a on the left so that their Lorentz forces add i.e. both are in the same direction. To reverse the direction of the motor force, the current direction is merely reversed in the coils. Since the magnet is the moving element in this motor, there are no flexing leads to break, unlike for example the voice coil motor used to actuate the diaphragm in loud speakers.

The weight of the motor 28 has been minimized using vanadium permendure magnetic material for both of the flux shells 22s,26s. This material was also used in the Philips cryo-refrigerators. Vanadium permendure can be magnetized up to 23,000 gauss thereby permitting use of minimum thickness shells to conduct the flux. The magnet, for example, puts out 5,700 gauss.

Pumping Action of Piston—This motor design has a hollow central core 26a to allow blood to pass through it. The check valve 24b which moves with the moving armature as shown in FIG. 2 is the outlet or aortic valve and is mounted to the right end of the piston as shown. When the piston moves to the right, it closes and blood is forced out. At this time, the left inlet valve 24a located in the stationary housing 22, is forced open permitting blood to flow into the pump. At the end of the stroke, the motor is reversed by reversing the current direction in the coils. This forces the armature back to the left or the starting point. As the piston starts back, the moving valve opens by the flow of blood forced through it as the inlet valve is simultaneously closing. This allows systolic outlet pressure to enter the motor on both sides so the motor can go back to the start position nearly free of any pressure across it. This introduction of systolic pressure also securely closes the inlet valve whose function is to eliminate back leakage of blood. Hence, the pump pumps blood unidirectionally from left to right through oscillation of the central piston.

Other linear motor designs that use this same-type configuration in cryogenic refrigerator compressors utilize one long coil that was sufficiently long for the stroke of the motor. This allowed the magnet always to be positioned under coil wire to develop a force throughout the length of the stroke. It was somewhat inefficient because coil power was wasted in non-force-producing parts of the coil. The present design is a major improvement. A long stroke was desired to minimize piston force and to maximize piston velocity, both of which increase motor efficiency. Instead of using one long inefficient coil, three short switchable coils are employed in two sets or groups. This way only those coils are turned on that directly surround the magnetic field and produce useful force. No heat is wasted in the other coils. With the use of one long coil in the cryogenic refrigerator application there was not a large waste of power because the stroke was relatively small compared to the magnet length. Consequently, the excess coil length beyond that of the magnet was not great so most of the coil turns were in the magnetic field. Efficiency did not greatly suffer. In this design, the magnet length is short to obtain a long stroke in a short length pump, and commutating the coils is required to maintain efficiency. It turns out (as discussed in Section C.) that 33% less power is lost using a 3 coil design over the use of one coil.

Rectangular magnet wire is used in this motor as a design refinement as was also used in the cryogenic refrigerators. Rectangular or square wire has a much larger fill factor than round wire. The coil volume is nearly completely filled with wire in order to make maximum use of the available space. This decreases coil resistance and increases motor efficiency about 18% over using round wire. By incorporating the new commutation scheme and using rectangular wire, motor power loss has been decreased a whopping 51% over conventional designs. Another advantage of rectangular wire is the excellent heat transfer obtained between coil layers. Full surface area contact results in maximum heat transfer; round wire would only have minimal line-to-line contact in comparison and coil temperature rise would be substantially higher.

As far as losses are concerned, the magnetic field is constant in the moving armature 26s. Hence, eddy currents and magnetic hysteresis (which is the magnetizing and demagnetizing cyclic loss associated with iron) is non existing. These losses only occur in the outer magnetic shell. They are very small, so laminating the outer shell or using eddy current reducing axial slots is not necessary.

Table 2 summarizes the motor specifications for a 45.7 mm linear motor 28 and pump 10 in an exemplary embodiment.

2. Efficiency Formula and Force Over Velocity Ratio

Efficiency Formulation—Motor efficiency is defined as the ratio of the mechanical output power to the electrical input power, $$\eta = P_{OUT}/P_{IN}$$

Since the only loss in the motor is the heat dissipated in the coil windings, $$P_{IN} = P_{OUT} + I^2 R$$

where, I=motor-current and R=resistance of the coil. The following assumptions are made:

1. Eddy currents are neglected.
2. Copper wire at 100° F. is used for the coils.
3. The entire armature of the motor is always within the active portion of the stator so that full overlap always exists between the magnets and coils.
4. The motor force constant is a true constant, independent of current or position.
5. Motor inductance is constant, independent of current or position.

Motor efficiency is given by:

$$\eta = \frac{1}{1 + \frac{(2.5 \times 10^7)\sigma\gamma}{(BH \times 10^6)Vm} \frac{F}{U}}$$

LEGEND
η=Motor efficiency (%)
BH=Energy Product of Magnets (Gauss-Oersted)
F=Motor force (lbs)
U=Armature velocity (in/sec)
Vm=Volume of magnets (in³)
γ=Coil resistance factor
σ=Magnetic field leakage factor For a given magnetic circuit design, the flux leakage factor σ is fixed. It corresponds to leakage of flux and flux not passing perfectly radially through the coil. The coil resistance factor γ is unity when corresponding to a coil of length equal to that of the magnet and always positioned in the field of the magnet. For the three coil design and using the proportioning of current in adjacent coils discussed in Section C, γ is equal to ⅔. In other words, the effective coil resistance of the 3 commutated coils is only ⅔ that of a single long coil. Motor efficiency does not depend on the number of coil turns. This determines operating voltage and inductance.

The BH or energy product of the magnets used is 33×10⁶ which is commonly referred to as 33 MGO. Standard neodymium iron boron magnets are available up to 40 MGO. The magnetic circuit of the motor, which includes coil radial thickness and other factors, determines the operating point of the magnet, or how much MGO it produces. The present design insures that the magnet is operating at its optimum energy product of 33 MGO.

Efficiency is proportional to the volume of magnet that is utilized, that is, the sum of the volume of the two magnet rings provided both are operated at the maximum energy product. This operating point is determined by the coil thickness and other geometric properties of the magnetic circuit.

Substituting for the constant parameters in the above equation, gives a very simple yet powerful formula for efficiency for the proposed motor of 45.7 mm diameter.

$$\eta = \frac{1}{1 + 1.05\frac{F}{U}}$$

For any given size motor, efficiency only depends on the Force over velocity ratio. That is why a large stroke was chosen (0.9 inch) as this minimizes this ratio and an efficiency of 85% could be achieved. Physiological constraints on pump length, to fit between the left atrium and descending aorta, were met using this stroke. The above formula accurately holds for the instantaneous energy conversion efficiency of the motor for the size shown. As can be seen, there are only two variables that affect motor efficiency. These variables are the force the motor puts out instantaneously, denoted by F, and the velocity U of the armature which is the piston. The ratio of F over U is the fundamental single variable determining efficiency. The smaller the force F, the higher will be its efficiency and F is minimized by using a large stroke. The larger the stroke, the smaller the diameter piston for a given desired stroke volume. Hence, the lower the force required to pump against systolic pressure. The longer the stroke, the greater the motor velocity possible for a given systole time. Thus, as long a possible stroke minimizes the F over U ratio and this maximizes motor efficiency.

A comment on the constant of proportionality (1.05) multiplying the F over U ratio. The larger the magnet volume and the higher the energy product magnet used, the smaller this constant and the more efficient the motor. Magnets possessing an energy product of 33 million were used, which is a conservative design since 35 MGO material is currently available. Use of higher strength magnets would minimally increase motor efficiency, but would require thicker iron cores to carry the extra flux.

As discussed in Section J on pump control, with piston position known from the position sensor 32, a constant systole velocity and a constant diastole return velocity can be maintained using a simple position and velocity feedback loop. This maximizes motor efficiency over the stroke since piston velocity is constant at its maximum value.

These motors are easily controlled, because they possess a constant force constant (force is directly proportional to current). That is why the motor current can be used as an accurate pressure transducer for physiological control of the pump. Furthermore, any desired waveform of systolic flowrate can be programmed, such as for example, sinusoidal pulse waveforms. In this case, the average motor velocity during systole and diastole would be 2/π as great as in the constant velocity case and motor efficiency would drop from the current 86% to 80%; still a very respectable value.

The use of three coils 28a or phases permits one to inject current only in the coils that produce force no matter how long the stroke. By choosing the axial length of each coil equal to that of the magnet ring, the piston stroke becomes an integral multiple of the magnet length (here 3 to 1) and the current in each coil can be optimally varied to minimize overall power consumption. This is a new and innovative way to commutate a voice coil linear motor winding.

At any instant of time, only one or two coils are positioned above a magnet ring 28b into which we want to inject current. If we choose the amount of current in each coil proportional to its amount of overlap with the magnet (in other words, coil current is proportional to wire length in the magnetic field), then the force constant of the motor remains constant (for ease of control), and the total current input to the motor is constant for a given output force. Thus, the control simplicity of the linear motor is maintained.

Figure 9:
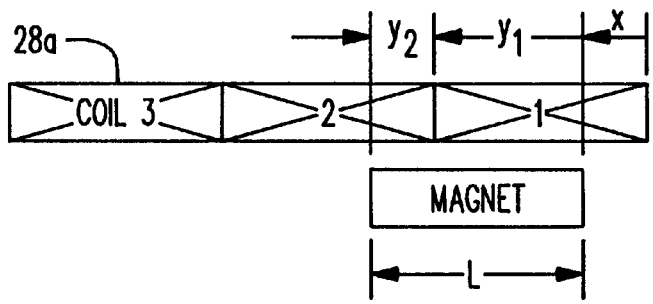
FIG. 9 is a schematic representation of three adjoining axial drive coils and cooperating magnet ring for use in deriving coil efficiency.

If this is done, the power loss of the motor will be ⅓ less than if the same total current was used in an ideal coil that could move along with the magnet to maintain its turns in the magnetic field. That this is true is derived as follows in connection with FIG. 9:

3.3-Phase Multicoil Advantages a. Efficiency and Commutation Derivation of Coil Efficiency Improvement LEGEND
x=magnet position
y=overlap of magnet on respective coil
R=resistance of each coil
L=magnet length=each coil length
$i_o$=current required in 1 coil with full overlap of magnet, to give force desired.
τ=time to reach stroke
  $y_1$=L-X (overlap on coil 1)
  $y_2$=X (overlap on coil 2)

Force=iLB
Force αiy and power=i²R in any coil
Constraint: Current in coil to be proportional to overlap y. This will give constant force throughout the stroke.

$$i_1 = \frac{(L-X)i_o}{L} \qquad i_2 = (X/L)i_o$$

As a check: $i_1+i_2=(1-X/L+X/L)i_o=i_o$, thus total current=$i_o$ as desired.

Derive Average Power Consumed over the stroke:

$$P_1 = (i_1)^2 R \qquad P_2 = (i_2)^2 R$$

$$P=P_1+P_2=R[(i_1)^2+(i_2)^2]=R(i_o)^2[((L-X)/L)^2+(X/L)^2]$$

$$P=[R(i_o)^2(L^2-2xL+2X^2)]/L^2$$

τ=time to reach "stroke L," and x=(ty/τ)L and substitute into P above:

Average Power $P_{avg}$ =

$$1/\tau \int_0^\tau P d\tau = 1/\tau(R(i_0)^2/L^2) \int_0^\tau [L^2 - 2L((t^2L/\tau) + (2t^2L^2/\tau^2)]dt$$

$$= R(i_0)^2/\tau L^2[L^2\tau - (2L^2/\tau)\tau^2/2 + (2L^2/\tau^2)\tau^3/3]$$

$$P_{avg} = 2/3 R i_0^2 \quad \text{Final Result}$$

If the motor were stationary with full overlap on one coil $$P=i_o^2 R$$

Thus, the assumed switching configuration is as though it had only ⅔ the normal coil resistance and dissipates 33% less power. If an infinite number of coils are used or if a single ideal traveling coil is assumed, coil resistance is R instead of ⅔R and motor efficiency is less. The assumed division of current proportional to overlap is therefore either optimal or close to optimal for minimizing power consumption.

General Implementation

The microprocessor controller 16 used for overall blood pump operation is to be used to compute the coil/magnet overlap y, using the position signal obtained from the magneto resistor sensor. With magnet overlap known and the direction of piston motion being specified, the appropriate currents $i_1$ and $i_2$, based on the above analysis are used in respective coils. The total current magnitude required at any instant is of course determined by a suitable feedback control loop to maintain the desired piston velocity.

b. Motor Redundancy

If all three of the coils 28a on one side of the motor became inoperable (either due to coil or electronic driver malfunction), the three coils 28a on the other side could take over at half the efficiency, and continue motor operation. Likewise, if two or only one coil should become inoperable, motor function can be preserved but at lower efficiency. To provide this redundancy the six-coils 28a can be individually driven each with their own driver. This is less reliable and more complex than the simpler option of series connection of each phase where only three drivers are needed.

Normally, the two right side coils 28a (phase 1) are connected in series, the two center coils 28a in series (phase 2) and the two left side coils 28a in series (phase 3). This gives the minimum quantity or three leads to commutate, one driver for each phase relative to ground.

If a coil in one of the phases is to be removed from the circuit due to a malfunction, such as shorting to ground, its series connection must be broken and the coil bypassed.

If needed, this fault detection and switching capability can be handled by the LVAD's microprocessor controller 16. The present thinking is that coil reliability is so high that the extra complexity and reliability concerns associated with fault detection may not be warranted. Providing backup or redundant transistor coil-drivers on the other hand, is easily implemented and providing space is available, is likely to be implemented.

c. Coil Geometry

Ideally, the motor coils 28a for the linear motor 28 are wound circumferentially around the magnet rings 28b. Axial force is produced by the cross product of the circumferential current and the radial flux from the magnets, and this force is slightly reduced if the current is not perpendicular to the flux.

In reality, geometrical asymmetries are created in the motor coil winding during its fabrication process. Of these, the most significant is the helical shape which results from having the coil progress along the length of the motor. Radial forces created by this asymmetry are relatively small. A torque is also produced, tending to rotate the piston tangential to the motor axis. This is undesirable because an independent motor winding is going to be used to provide unidirectional rotation.

Figure 10:
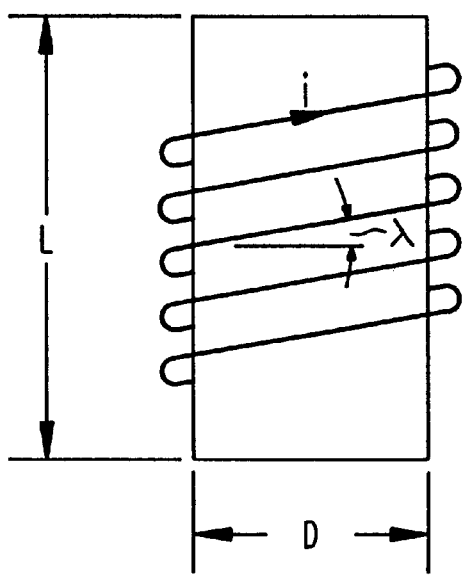
FIG. 10 is a schematic representation of a helical coil winding for an exemplary drive coil used in the linear motor.

The FIG. 10 is a schematic of a typical motor coil of diameter D wound on a cylindrical surface of length L. The number of turns is N with a helical wind angle λ.

Figure 11:
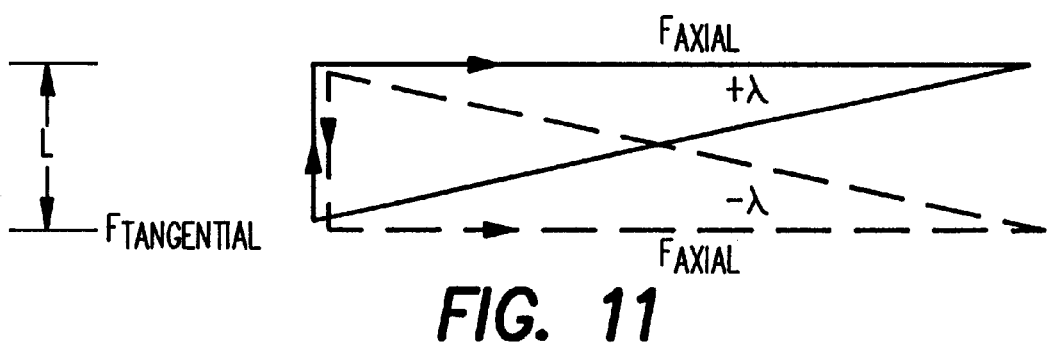
FIG. 11 is a schematic representation of forces produced by the drive coil for two opposite helix winding angles.

The coil current i can be thought of as flowing in the axial direction through a length and circumferentially through a length NπD. The forces produced by these currents are shown schematically in FIG. 11. The circumferential current produces the desired axial force, whereas a tangential force is produced by axial current. This tangential force which is calculated to be quite small, nevertheless, tends to spin the magnet armature like that of a rotary motor; first in one direction, then in the other as motor current is reversed. If an even number of winding layers is used, and the coil 28a is wound such that adjacent layers have opposite helix angles, then the current i in each layer will be oppositely directed along the length L, and their respective tangential forces will cancel which is the configuration of the coils 28a in the preferred embodiment. Hence, no torque will be produced. As shown in FIG. 11, the axial forces add as desired.

If the winding does not have an even number of layers, torque cancellation cannot occur and the independent rotary winding would have to compensate. For this reason, the motor 28 best uses an even number of layers.

Section C—Commutation

As shown in FIG. 2, the drive coils 28a are disposed in two symmetrical sets of three drive coils 28a at opposite ends of the housing 22. And, suitable means in the form of the controller 16 are provided for commutating electrical current into respective ones of the drive coils 28a for magnetically translating the piston 26 in the axial forward stroke from the housing inlet to outlet 22b,c, and in turn in the axial aft stroke from the housing outlet to inlet 22c,b for oscillating the piston 26 in the housing 22 to cyclically pump the blood axially therethrough. The controller 16 is operatively joined to the drive coils 28a through suitable electrical leads for sequentially supplying electrical current thereto for axially oscillating the piston 26.

In the preferred embodiment illustrated in FIG. 2, the drive coils 28a and the magnet rings 28b have equal axial individual lengths so that stroke of the piston 26 is an integer multiple of the magnet ring length. The controller 16 is suitably configured to supply electrical current to the drive coils 28a proportional to the amount of overlap of the drive coils 28a with the magnet rings 28b as described above for minimizing power consumption.

The commutating means further comprise the position sensor 32 in accordance with an exemplary embodiment mounted in the housing 22 adjacent to the piston 26 for determining axial position of the piston 26. The position sensor 32 is operatively joined to the controller 16 for providing position of the piston 26 thereto for commutating the drive coils 28a. The axial position sensor 32, or transducer, is further described below in accordance with an exemplary embodiment.

Section D—Axial Position Transducer

1. Magneto Resistor Sensors

Magneto Resistors (MR) 32a are very small, about ¼ mm thickness×1 mm×2 mm solid state variable resistors. The MR 32a is usually composed of a ceramic substrate onto which is sputtered a thin film in a meandering pattern of nickel antimonide and indium antimonide. A typical resistance is 50 ohms.

Figure 12:
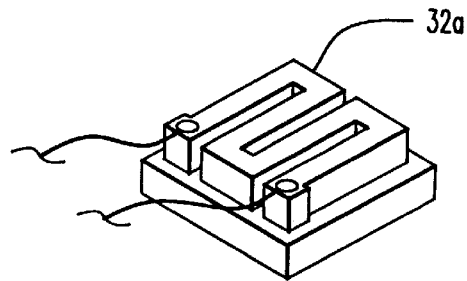
FIG. 12 is a schematic representation of an exemplary magneto resistor on a substrate for use in a position sensor for determining axial position of the piston within the housing illustrated in FIG. 2.
Figure 13:
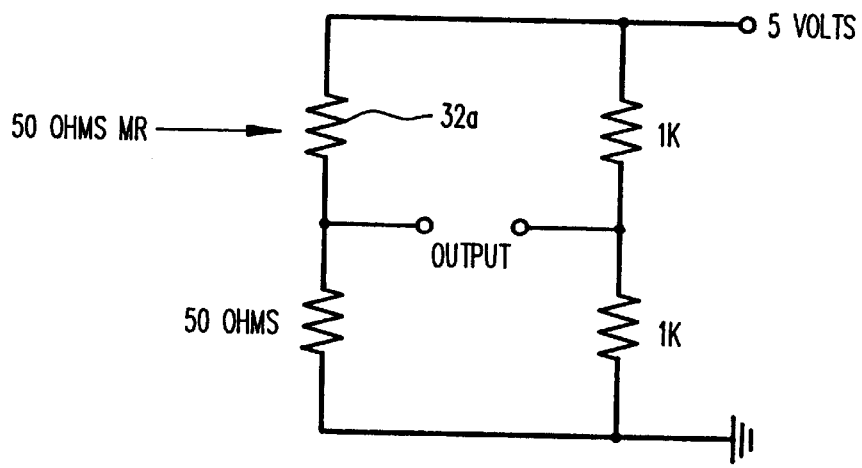
FIG. 13 is an exemplary magneto resistor circuit for the magneto resistor illustrated in FIG. 12 for use in configuring the position sensor.

FIG. 12 is a schematic of a typical MR (Ref. Siemens Galvanometric Handbook, 1976/77, pages 52–53). In the presence of a magnetic field, the resistance of the MR 32a increases dramatically. It is this property that lends itself to use as a position sensor 32 in many applications. MR's do not wear out or age. They do not require oscillators or complex electronics unlike variable differential transformers (LVDT) or eddy current sensors. They only require a 5 or 10 volt D.C. input voltage. When used in a simple bridge circuit, output is several volts and no amplification is required. A typical bridge circuit incorporated in the controller 16 is shown in FIG. 13. Reliability of a circuit this simple is extremely high.

MR's have been available and used for two decades and are known for their high reliability and durability. MR's are readily available from Kangyo Denki Ltd., Siemens and others. IBM makes extremely small ones for readout of data on sliders in hard disc drives. They are also inexpensive.

Figure 14:
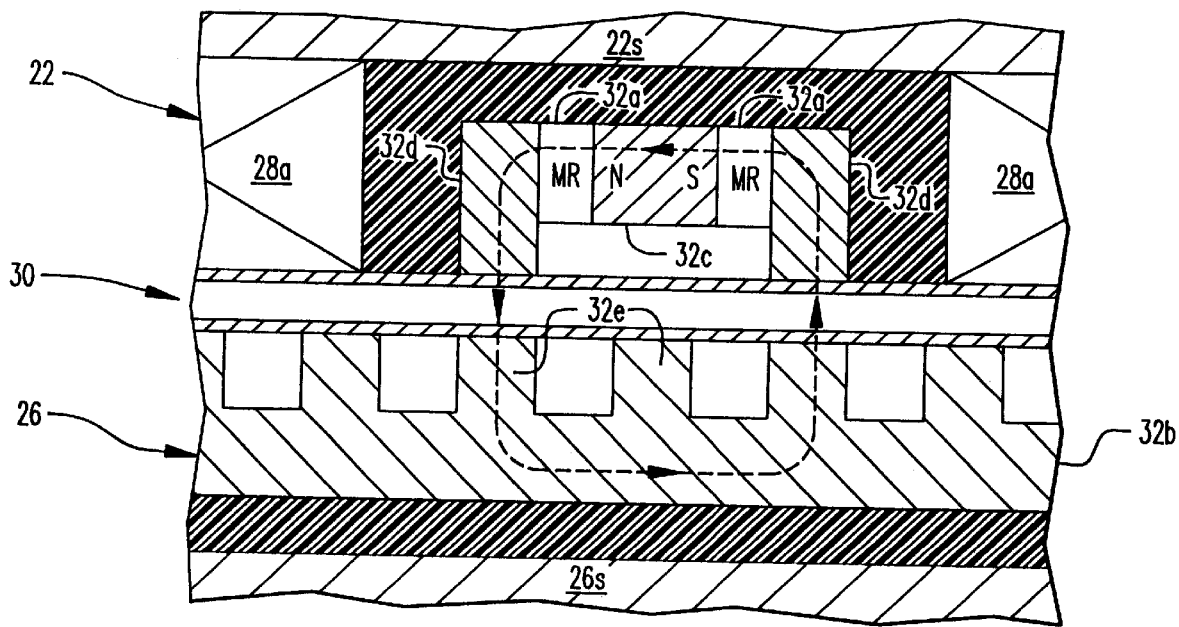
FIG. 14 is an axial sectional view of an exemplary embodiment of the position sensor shown in the pump of FIG. 2 illustrating the magnetic flux path between the magneto resistor and cooperating position sleeve around the circumference of the piston for determining the axial position thereof.

FIG. 14 shows how MR's are used to produce a sine wave or digital output pulse train as the piston 26 moves in the housing 22. By counting the number of pulses from the home or start position, instantaneous position is determined.

The Magneto Resistor (MR) 32a is shown in conjunction with a redundant MR 32a sandwiched between a small magnet 32c and two thin iron pole pieces 32d. The magnet biases the resistor to operate at a high gain point. The magnetic flux produced travels down the tiny outer pole piece 32d and into the inner poles 32e that are defined between circular grooves cut into the iron sleeve or ring 32b. The outer and inner poles 32d,e are shown aligned in the figure. Under this aligned condition a minimum reluctance path exists so that a maximum of flux passes through the MR 32a. MR resistance is now a maximum which gives a typical bridge output signal of 3 volts. As the piston 26 displaces, the poles misalign and less flux travels through the MR. This decreases MR resistance and wheatstone bridge voltage drops to typically 1 volt. Output voltage is a minimum when the pole pieces 32d,e are fully misaligned, the pole of one aligned with the valley of the other.

When the piston travels a distance of 1 pole pitch, here shown to be 0.040", one pitch cycle is completed. Thus one pulse occurs every pitch or 0.040". The actual variation is close to sinusoidal for the geometry shown.

The position sleeve 32b illustrated in FIG. 14 is mounted coaxially in the piston 26 around the armature or shell 26s by using a suitable epoxy and extends axially between the spaced apart magnet rings 28b as illustrated in FIG. 2. A sufficient number of the inner poles 32e are formed in the position sleeve 32b for allowing the position sensor 32 to count the poles 32e over the entire axial stroke of the piston 26 within the housing 22.

As shown also in FIG. 2, a second one of the position sensors 32B is also operatively joined to the controller 16 and cooperates magnetically with the common position sleeve 32b. The second position sensor 32B may be identical to the first sensor 32 except that it is preferably displaced 90 electrical degrees or one quarter pitch from the first sensor 32 for determining axial direction of piston movement in the forward and aft strokes.

Using the second MR and magnet sensor assembly 32B allows the determination of piston motion direction. This second sensor is displaced 90 electrical degrees from the first which is 0.010" in this example. Its output sine wave phase either leads or lags the first from which respective direction is determined. Standard miniaturized circuitry exists to determine position and direction from these quadrature signals as this is the standard pulse train output of optical position encoders and resolvers. (Ref. "Magnetoresistive Sensors and Magnetic Encoders for Motion Control", P. Campbell, Princeton ElectroTechnology, Inc., Sensors Magazine, May 1989). Position resolution is ¼ the pulse pitch by adding both signals. So a position resolution of 0.010" is available from the geometry used in this example.

The standard circuitry will also interpolate position between sine wave peaks so that at least 10× more resolution is available. This degree of accuracy is not required.

The use of 0.020" thick pole pieces is dictated by the overall gap size of two titanium can thicknesses. For 0.020" thick poles the useful bandwidth is 6 Khz before eddy current generation becomes a problem. At a speed of 18 in/sec during systole, the resulting pulse frequency is only 18 divided by 0.040 pitch=450 Hz, which is relatively low.

It is desirable that the pulse counter be zeroed every cycle to eliminate the possibility of error accumulation if a pulse should be missed. This is done by using another MR located at the end of travel position (not shown). It will provide a "home" pulse at the end of travel. It is very easy to achieve MR redundancy in both the pulse wave train location and at the end of travel location. Two MR's are merely used sandwiched in the magnetic circuit as shown in the previous figure. No extra space, pole pieces or magnets are required.

Slight drift in MR output with temperature variations will have no effect on position accuracy. It is not the signal amplitude that is used but the number of pulses. The presence of small extraneous magnetic fields from the motor magnets is not expected to appreciably affect the pulse producing magnetic circuit of the MR; since Magneto Resistors operate up to 3,000 gauss. They have been used successfully for position sensing by IBM under similar conditions in a printer carriage drive linear motor.

Section E—Spinning Piston

Figure 15:
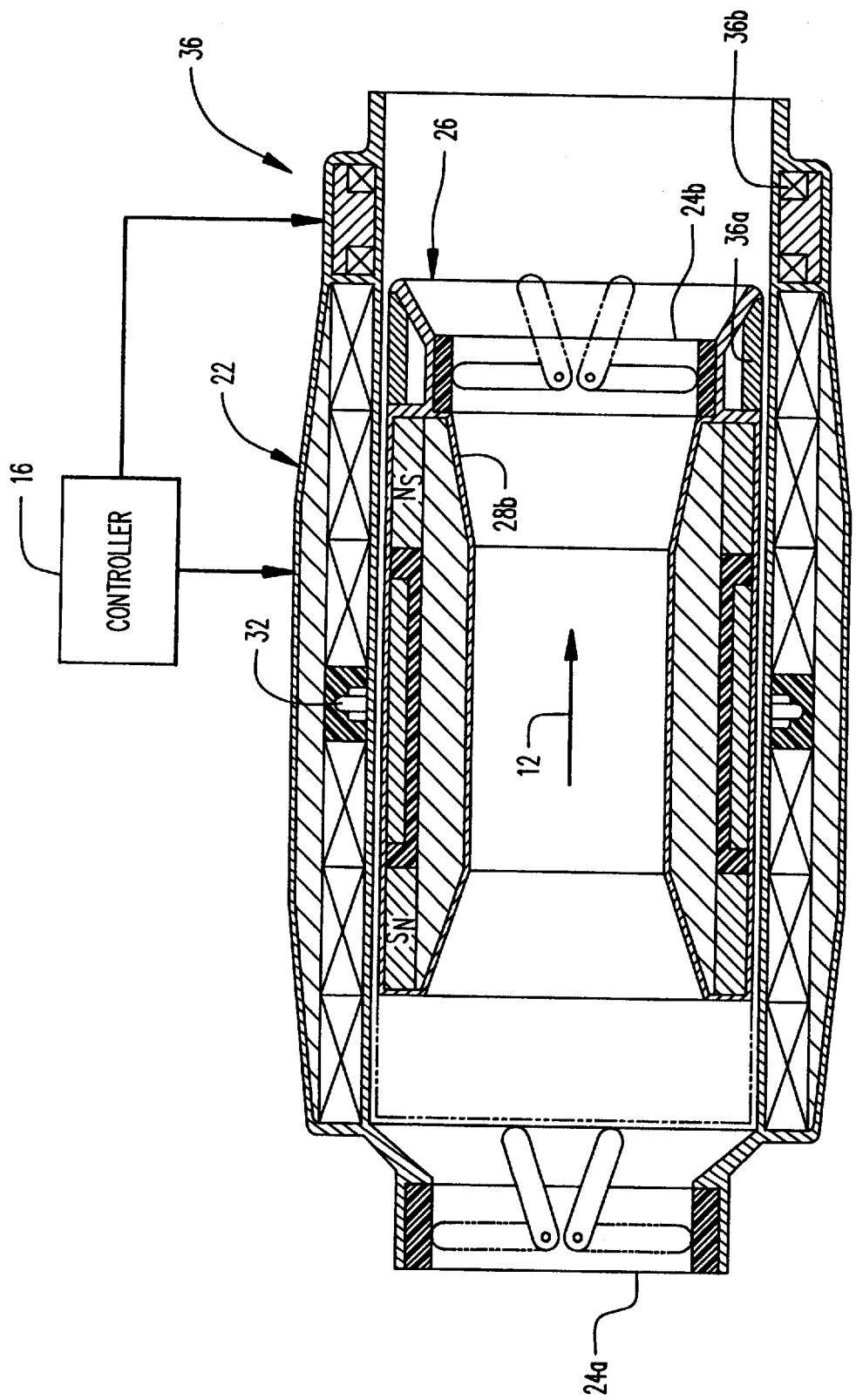
FIG. 15 is a partly sectional and schematic axial view of the linear pump illustrated in FIG. 2 in accordance with an alternate embodiment including an independent rotary motor for spinning the piston inside the housing.

As indicated above, the piston 26 illustrated in FIG. 2 is suspended all around on a bearing film of blood in the gap 30 which also acts as a clearance seal for the piston 26. In order to support the piston 26 in a rotary journal bearing, it is desirable to provide suitable means for rotating or spinning the piston 26 for circumferentially developing hydrodynamic pressure in the bearing fluid, with the bearing thereby defining the journal bearing. In one embodiment illustrated in FIG. 15, an independent brushless DC rotary motor 36 is disposed at one end of the piston 26 and housing 22. The rotary motor 36 may take any conventional form and is operatively joined to the controller 16. For example, the rotary motor 36 includes an annular rotor magnet 36a in the form of a ring disposed in the aft end of the piston 26 which has a plurality of circumferentially adjoining rotor poles. A cooperating stator band 36b includes a plurality of circumferentially adjoining rotary-drive spin coils fixedly disposed in the aft end of the housing 22 for magnetically cooperating with the rotor magnet 36a for rotating the piston 26.

Only when the piston 26 overlaps the stator winding band 36b is torque imposed by the rotary motor 36. Thus torque pulsations are imposed whose cycle average is the desired average torque. The stator coils or phases surround the piston's armature magnet 36a. They are sequentially commutated by the controller 16 to produce a rotating magnetic field. This rotates the piston. The motor 36 may be commutated using available chips to monitor the back EMF thereby eliminating hall effect or other rotary position sensors needed for commutation. The rotation of the piston causes it to become a journal bearing with load capacity. Due to the constant torque input, its resulting RPM self regulates depending on blood viscosity. Bearing load capacity is then shown to be invariant with blood viscosity. Disadvantages of this design are pulsatile torquing which gives small but acceptable torsional vibration, and a slight increase in pump weight and axial length. To start the piston 26 revolving a high input current pulse is injected to overcome rubbing friction until the bearing lifts.

Figure 16:
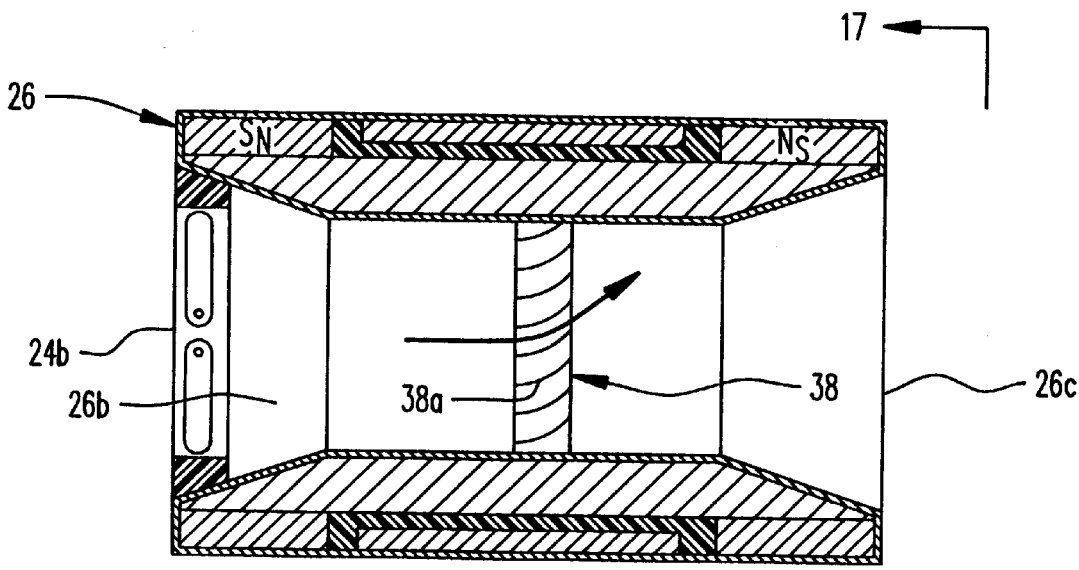
FIG. 16 is a schematic representation of the pump piston illustrated in FIG. 2 in an alternate embodiment including a turbine disposed in the bore thereof for spinning the piston inside the housing.
Figure 17:
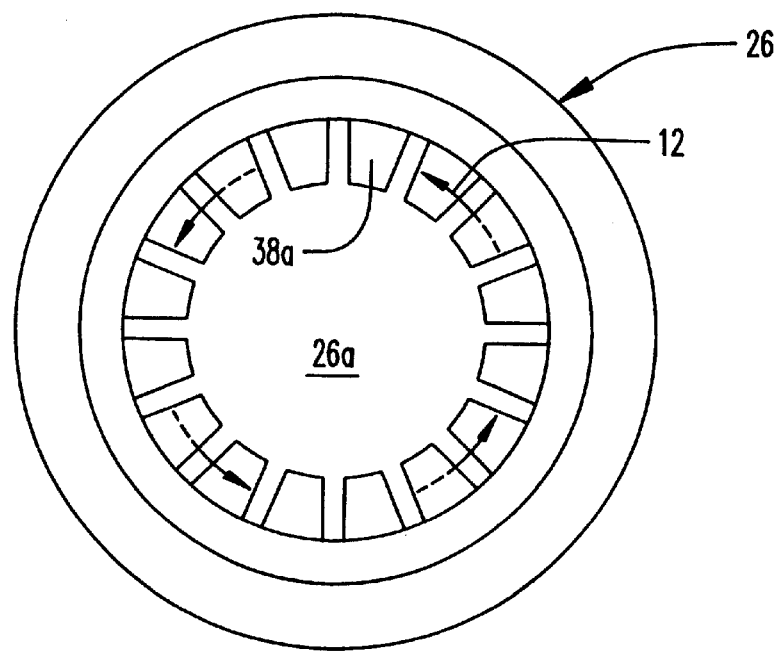
FIG. 17 is an end view of the piston illustrated in FIG. 16 taken along line 17—17.

A second method for piston rotation is to employ a miniature axial flow turbine 38 as shown in FIGS. 16 and 17. A plurality of circumferentially spaced apart turbine vanes 38a are attached to the piston 26 and driven by the flow through its bore 26a. Upon piston reset, the bore flow impinges on the vanes imparting rotation to the piston. This eliminates the need for a separate rotary motor. Upon aft, reset travel of the piston 26, the blood engages the vanes 38a to cyclically rotate the piston 26.

When used with the turbine 38, the piston's check valve 24b is preferably located ahead of it in the piston inlet 26b, and the turbine is located downstream preferably near the piston's outlet 26c. This eliminates reverse torque on the piston caused by swirling flow at the turbine outlet which would impinge on the open valve producing counter torque.

Average rotation speed using a turbine 38 also self regulates with viscosity because turbine torque depends on blood density and blood velocity through it, not on viscosity. The primary advantage of using a turbine is the elimination of the rotary motor 36 and associated extra electronics. When a turbine is used, average piston torque can also be kept constant just like when employing a rotary drive motor. To accomplish this, the piston reset speed is varied to allow the product of torque and reset duty cycle (input energy from the turbine) to remain constant each cycle. In other words diastole time is varied depending on overall cycle time. This necessitates having the piston axial motion dwell whose duration will be a function of flowrate. This dwell is ideally done at the home position.

The desired diastolic reset time and dwell as a function of net flowrate for the 45.7 mm pump are shown in Table 3. This was computed based on the cycle periods for each flowrate listed.

The vane turbine angle shown in FIGS. 16 and 17 is chosen to give the desired rpm based on the maximum flowrate of the pump which gives the minimum diastolic time expected. In this case it computes to be 14 degrees which is a relatively small angle and will not greatly swirl the flow exiting the turbine. This will create low turbulence and not cause blood damage. The formula used to derive the variable diastolic times required to produce constant average torque, and used to compute $\tau_d$ for constant turbine torque on average over a cycle is:

$$\tau_d = (4.44 \times 10^{-3})/(\tau + 0.010)$$

In order to start the piston spinning during implantation, about 10 times the average running torque is needed. The turbine puts out about twice the average running torque at a reset time of 0.043 sec see chart at maximum flow. An additionally needed factor of 5 is obtained by using a reset time of about 20 msec. Once the piston is up to rotation speed, normal reset times are used.

Figure 18:
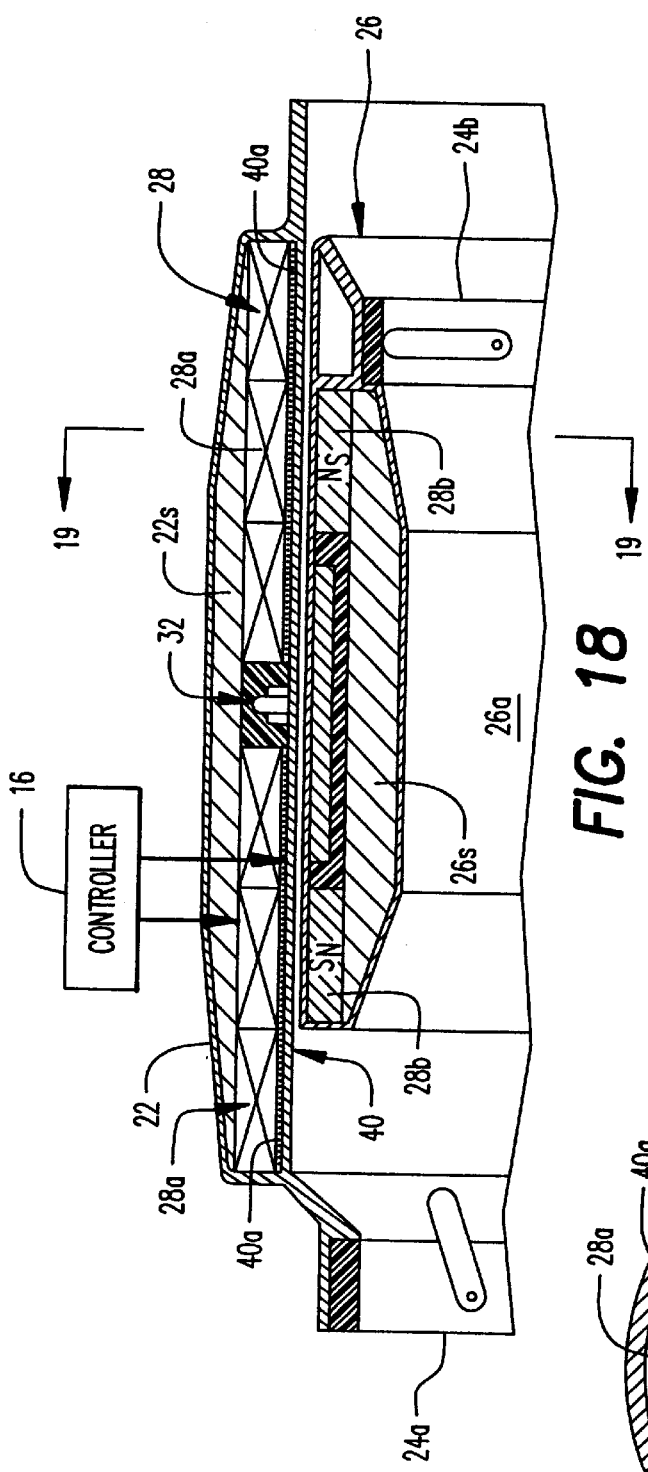
FIG. 18 is a partly sectional and schematic axial view of a portion of the linear pump illustrated in FIG. 2 in accordance with another embodiment of the present invention including an integral rotary motor disposed radially below the axial drive coils in the housing for spinning the piston simultaneously with axial reciprocation thereof.
Figure 19:
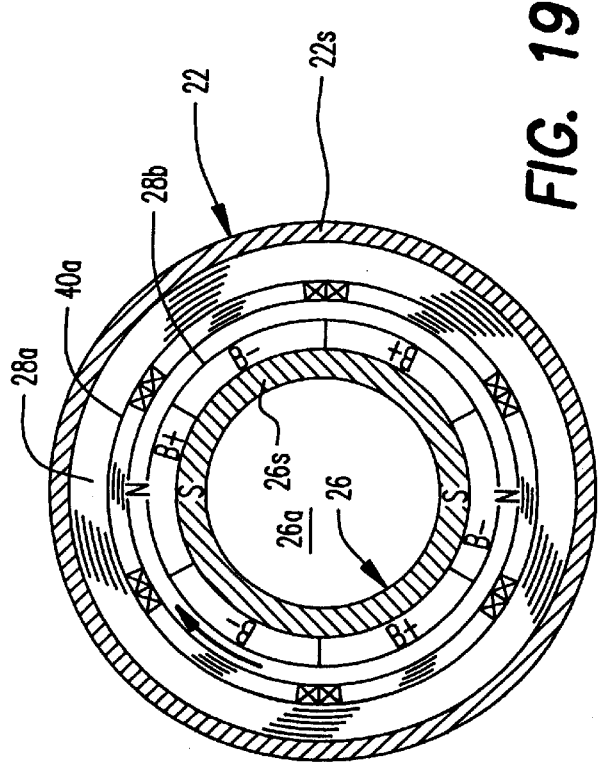
FIG. 19 is a radial sectional view of the linear pump illustrated in FIG. 18 and taken along line 19—19.
Figure 20:
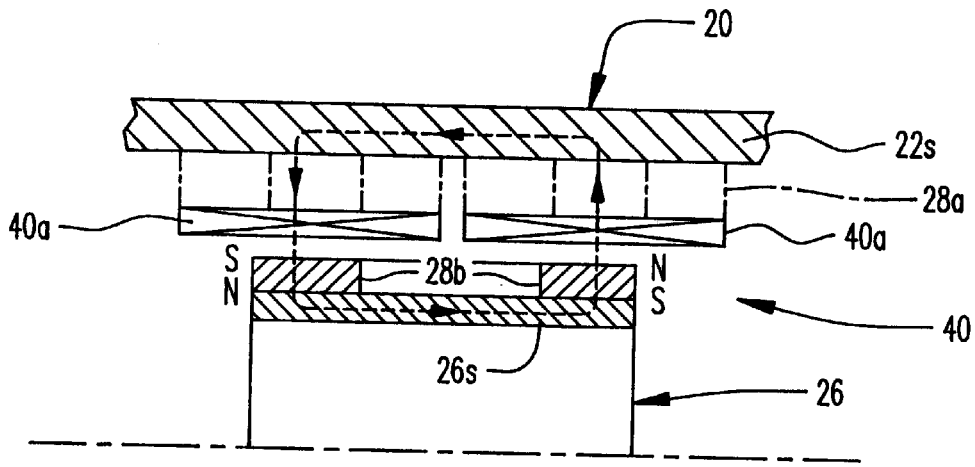
FIG. 20 is a schematic representation of the integral rotary motor illustrated in FIGS. 18 and 19 for spinning the piston inside the housing.

Another rotary motor alternative is incorporated into the linear motor 28 itself. This is shown in FIGS. 18–20. An integral brushless DC rotary motor 40 includes a pair of axially spaced apart stator bands 40a each having a plurality of circumferentially adjoining rotary-drive spin windings or coils disposed inside the housing 22, and radially below respective ones of the axial drive coils 28a. In this embodiment, the two magnet rings 28b have circumferentially spaced apart zones of different magnet field flux density designated B+ and B− as shown in FIG. 19. This may be accomplished by suitably slightly demagnetizing the circumferential zones around the perimeter of the magnet rings 28b to create relatively high and low flux density zones for defining corresponding poles. The zones are axially aligned in a common plane, and positioned radially below respective ones of the stator bands 40a for being magnetically rotated thereby. Each of the stator bands 40a as shown in FIG. 18 is disposed axially coextensively with a respective one of the symmetrical sets of three-drive coils 28a, and radially inwardly thereof for simultaneously axially translating and circumferentially rotating the piston 26 in the housing 22.

A rotating magnetic field is set up by stator phases (similarly as in the above rotary motor 36) but they are located at the I.D. of the axial drive coils 28a. In order to produce rotation using the existing magnet rings, the rings are slightly demagnetized at three places around the circumference thereby creating six alternating zones of higher and lower magnetic field. This creates greater and less alternating flux to link with the drive coils of the bands 40a producing an EMF in the coil, and motor work can be done. The armature fields interact with the three phase stator coils of the bands 40a in exactly the same way as the previous brushless DC motor 36. These phase windings can be very thin 0.010" thick in a single in-plane layer of turns in band 40a because the motor 40 need only put out low power (typically 60 mw) when rotating, and coil ohmic efficiency does not have to be great.

To start up the piston 26 a short duration impulse of high current is employed by the controller 16 to generate about ten times more torque to overcome piston/bore friction. Incorporating the rotary motor 40 into the linear motor 28 requires virtually no added axial space or weight. It is also redundant since windings at each magnet ring 28b can be used. Both windings 40a could be used for starting where high torque is required. Stator return flux is small due to the low torque required. This flux is carried circumferentially by the outer return shell 22s of the linear motor.

In an alternate embodiment, the stator bands 40a may be instead located radially above the axial drive coils 28a. In either embodiment, the bands 40a are radially aligned with the drive coils 28a for allowing simultaneous axial translation and spinning of the piston 26.

Homopolar LVAD Piston Motor

The LVAD piston 26 is to be rotated using ideally a constant average torque. A distinct advantage in packaging exists if the existing linear motor magnets are utilized for rotation as well. This eliminates the need to position a brushless D.C. motor at one end of the piston that requires additional axial length and results in a pulsatile torque to the piston; the torque being introduced near one end of the stroke. A more smooth nearly continuous torque can be provided with the disclosed motor and no additional axial length is needed. Its efficiency is comparable or better.

Each magnet ring 28b of the linear motor 28 is radially magnetized either as a solid ring or by bonded segments. The linear motor requirement is for a uniform radial magnetic field or one which is circumferentially symmetric to minimize magnetic radial instability and tilt forces with the stator. This is satisfied in the rotary motor modification needed to the magnet rings.

As shown in FIG. 19, each magnet ring 28b is selectively demagnetized about 10% in equally spaced angular regions around the circumference. This creates unidirectional field poles which in the analysis are assumed sinusoidal but may be of any symmetric variation. The mathematical effect is a "reversing" magnet field imposed on a constant magnetic field and this induces a back EMF into the stationary drive coils 28a producing torque on the magnet. A standard three phase winding in the bands 40a at each end of the motor 40 can be used. The motor 40 is called homopolar because the real field does not change radial direction from pole to pole, it only does so mathematically.

Long coil bands 40a above each magnet ring 28b ensure that the flux from each magnet segment enters the coil independent of axial piston position. Thus, torque is constant with axial position of the magnet ring. This does not make for efficient use of the coil but is not important in this blood pump application because the rotary power requirements are so low. Motor torque is proportional to winding current so the torque is easily controlled. The more a magnet segment is demagnetized $\Delta B$ to create a circumferential flux variation the stronger the torque for a given current, and the thinner radially the coil can be for a given efficiency. For a flux variation $\Delta B$ of about 10% very little effect on linear motor efficiency will occur and this can be compensated if desired by using stronger Neodymium magnets.

The disclosed motor is a brushless D.C. motor which may be commutated using rotation sensors or back EMF circuitry which is standard such as for disc drives. FIG. 20 illustrates the rotary motor 40 schematically. The left and right coils of the same phase can be connected in series to double the applied voltage if desired.

Section F—Piston Journal Bearing Design

1. Determining Loads Imposed on Bearing a. Motor Radial Instability

Moving magnet motor armatures are inherently radially unstable because the magnet structure is attracted to the surrounding stationary ferromagnetic material. This geometry is shown in FIG. 8. If the magnet ring 28b is displaced radially, it moves closer to the stator iron; consequently, the radial force increases in the displaced direction. At the true magnetic center (approximately equal piston gaps), these forces are perfectly balanced.

With the magnet ring displaced, asymmetry in the magnetic gap reluctance produces an associated change in the magnetic field. With the armature displaced from magnetic center, the reluctance decreases with the decreasing gap and increases in the diametrically opposite increasing gap. The flux density in the gap increases with the lower reluctance, decreases with the higher reluctance, and produces a net side force. Consider FIG. 21 which shows nonconcentric ferromagnetic cylinders displaced radially by an amount e. The local reluctance of the magnetic circuit at $r_1$ is lower than that at $r_2$.

Figure 21:
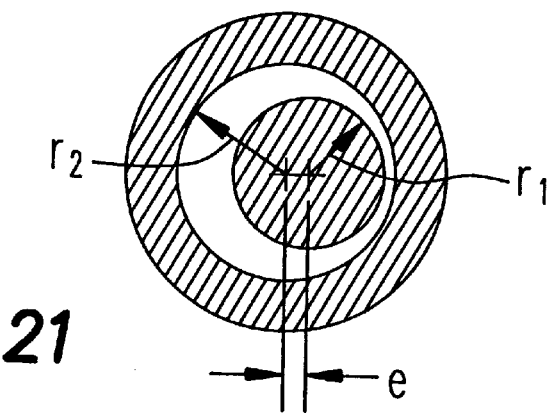
FIG. 21 is a schematic representation of a pair of non-concentric cylinders forming a general bearing to show radial instability thereof.

The geometry depicted in FIG. 21 is magnetically the same as that of the rotary motor 40. Since permanent magnets 28b are attached to the inner cylinder or shell 26s, a radially nonsymmetric field results when the motor armature moves radially. The side force produced by this field is a function of the displacement. Analysis predicts that a low force is inherent in the combined linear/rotary motor 28,40 design because of the relatively large effective gap between the stator iron shell 22s and the magnets 28b.

b. Motor Side Load

Strength Nonuniformity of Motor Magnets

The magnet rings 28b of the motor will have a small degree of magnetic field strength asymmetry. In other words, the radial magnetization could be slightly more on one side than another. Hence, it will attract the stator iron shell 22s more on one side than another which produces a net side load on the piston. This asymmetry can be minimized by constructing the magnet ring of an equal number of magnet segments and positioning matched pairs of equal strength segments opposite one another. In this way, a uniformity of 1.5% or better is achievable. This was the method of construction used in the cryogenic refrigerator motor to minimize side loads on the magnetic bearings. Since that time, it now appears possible to construct the magnet ring 28b in one piece and radially magnetize it. Its strength uniformity should be excellent. If this needs to be improved, selective areas can be slightly demagnetized to bring the ring into conformance. If this proves possible to do, the manufacturing cost of the rings will be substantially reduced.

Figure 22:
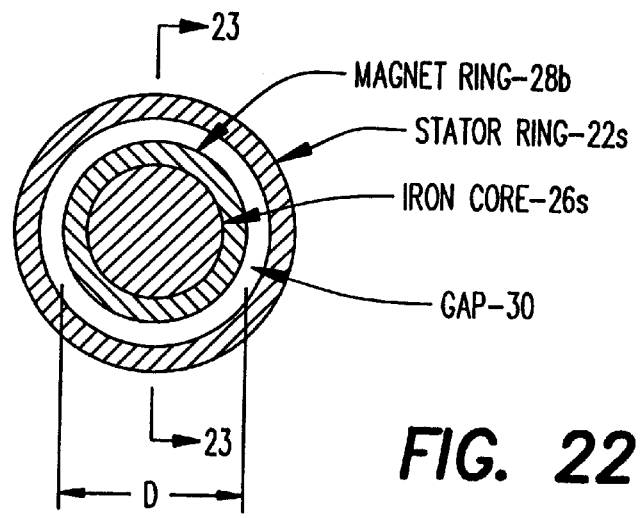
FIG. 22 is a radial section through an exemplary magnetic circuit schematic of the pump having a spinning iron core within a stationary stator iron.
Figure 23:
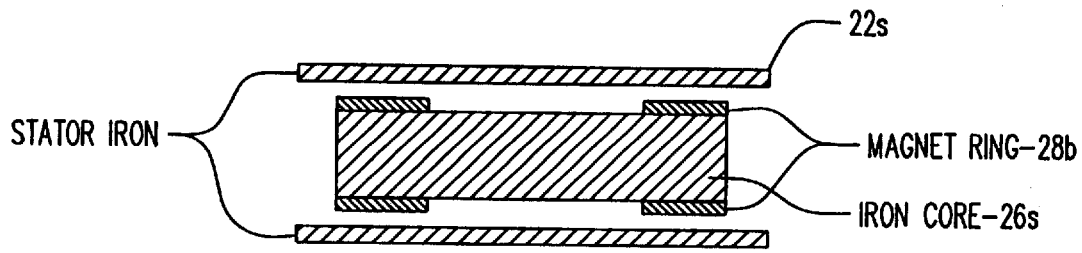
FIG. 23 is an axial cross section of the schematic pump illustrated in FIG. 22 and taken along line 23—23.

FIGS. 22 and 23 are schematic cross sections of the motor. The magnets 28b are attached to the center Permendure core 26s which moves. Only an outer piston gap 30 exists. Two magnet rings compose the armature.

2. Design Point—General Comments

In the design of a journal bearing, the fluid viscosity is an important parameter. Oil and other lubricants used to lubricate journal bearings are Newtonian fluids. Their viscosity is constant and not a function of shear rate. With viscosity constant, the design of the bearing is straight forward.

Viscosity is the constant of proportionality allowing calculation of shear stress if the fluid's rate of shear is known.

$$T_{xy}(\text{shear stress} = \mu(\text{viscosity})du/dy$$

where du/dy is the shear rate or rate of change of velocity with position in the fluid. This is used later in Section H. The usual fluid mechanical assumptions of constant viscosity or Newtonian behavior can be reasonably assumed in many problems, if the correct blood viscosity is used. The viscosity of blood depends on shear rate, as shown in FIG. 24 reproduced from Chemical Engineering in Medicine and Biology, Hershey, Plenum Press, p. 67, 1967.

Figure 24:
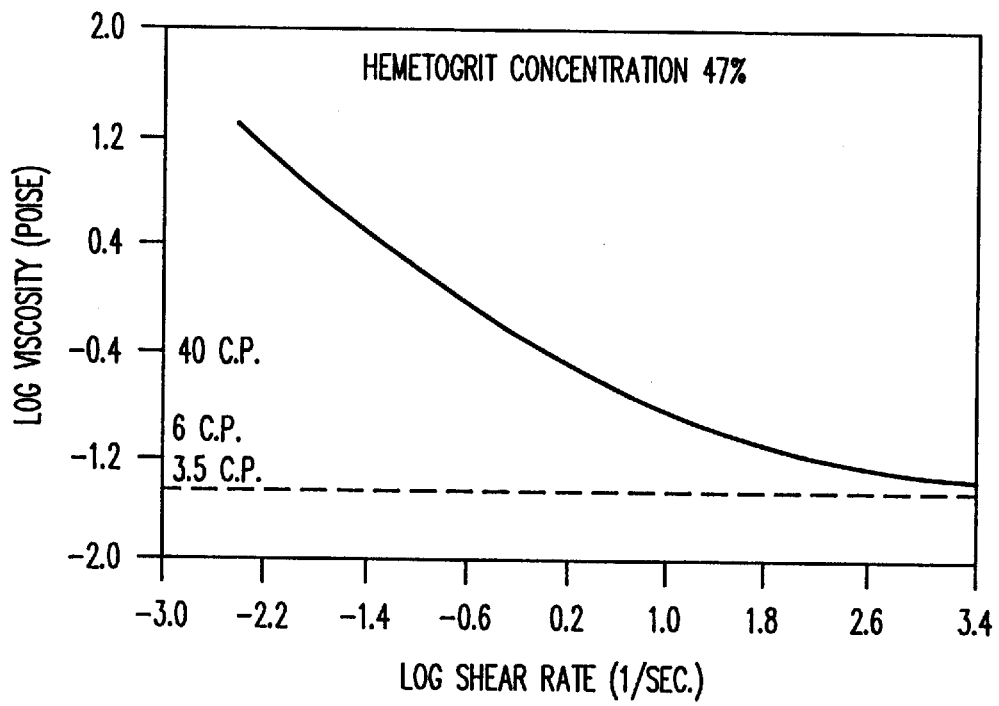
FIG. 24 is a graph plotting blood viscosity as a function of shear rate.

As can be seen from FIG. 24, for shear rates in excess of about 100 $sec^{-1}$, which is very low (log shear rate=2.0 or above), the viscosity of blood is nearly constant and decreases slightly as shear rate increases. Since the shear rate existing in the bearing is greater (as is the shear rate in ones heart, aorta and virtually all areas in an LVAD device), the minimum viscosity of blood can be used for calculation purposes. This value as shown is 3.5 centipoise. Indeed, water glycol or other solutions of this viscosity are used in mock circulation loop and other in vitro studies to simulate the hydrodynamical properties of blood.

The use of 3.5 c.p. for blood viscosity is commonly accepted and is conservatively used to design the bearing. It turns out, as will be proven in Section G, that the value assumed for viscosity is not critical when a constant torque is imposed on the bearing to create rotation.

Section G—Bearing Load Capacity Invariance With Blood Viscosity

1. Constant Torque Input Requirement

Viscosity invariance is very desirable because the patient's effective blood viscosity can change with medication, hematocrit content, etc. The same pump can be used with all patients under all circumstances by applying a constant torque to the bearing.

When a constant current is placed in the rotary winding 40a of the rotary motor 40, a constant torque rotates the bearing. Therefore, if blood viscosity decreases for any reason, such as the application of drugs, drag torque decreases and the bearing speeds up on its own.

2. Major Advantages

Load capacity is independent of the patient's blood viscosity and bearing RPM, so the same design point is applicable to all types and kinds of people's blood. The load capacity is constant or invariant and depends only on the input torque, not on viscosity or operating RPM. The same bearing eccentricity ϵ, will also result as the original design value for the same load. This is a powerful advantage as it says that bearing RPM sensors and speed controls are not needed. A simple constant input current is set for the desired design value of torque or RPM and nothing further need be done. The bearing speed will compensate for viscosity on its own. This is all done via "mechanical feedback".

Major Advantage for Implantation Simplification

A saline solution of water will be used to purge the pump of all air when implanted. This solution is ⅓ as viscous as blood so the bearing, when started, will run at 72×3=216 RPM to retain its design load capacity. As the saline is purged away and replaced by blood, speed will stabilize at 72 RPM. This results with a factory preset input current which needs no adjustment during implantation.

3. Bearing Washout Time

During systole the linear motor 28 pumps against 120 mmHg=2.32 psi. This creates an additional transient flowrate through the bearing. It is desirable to have this flow in the same direction as the viscosity pump flow so they don't fight one another and bearing washout remains unidirectional. This is accomplished by placing the screw pump 34 on the outlet side of the pump as shown in FIG. 30.

The oscillating axial motion of the bearing will induce equal hydrodynamic flow volumes in each direction with a net of zero. One therefore ignores this effect.

Volume of blood in bearing gap=$\pi DhL$ $$v_b = \pi(1.274)(1.5 \times 10^{-3})(2.00)$$

$$v_b = 1.2 \times 10^{-2} (in^3)$$

Volume of blood delivered to bearing
From previous screw pump design:

$$Q\text{ pump} = 1.45 \times 10^{-3} \text{ in}^3/\text{sec}$$

systole flow:

$$Qs = \pi Dh^3/12\mu \Delta Ps/L$$

$$Qs = \frac{\pi(1.272)(1.5 \times 10^{-3})^3}{(12)5.1 \times 10^{-7}} \frac{2.32}{2.00} = 2.56 \times 10^{-3} \text{ (in}^3/\text{sec)}$$

$$Qs \text{ average volume delivered during 1 cycle} = Qs \frac{\tau \text{ systole}}{\tau \text{ cycle}}$$

τ cycle typical=0.168 sec at 6 L/m (6 Hz)
τ systole=0.055 sec $$Qs = 2.56(10^{-3}) \frac{.055}{.168} = .84 \times 10^{-3} \text{ (in}^3/\text{sec)}$$

Total volume pumped=(Q pump+Qs) t where t is washout time (sec) Volume of bearing=Vb $$t = \frac{Vb}{Q\text{ pump} + Qs} = \frac{1.2 \times 10^{-2}}{(1.45 + .84) \times 10^{-3}}$$

$$t = 3.0 \text{ sec or 18 pump cycles}$$

New fresh blood is replenished every 3 sec or 18 pump cycles in an exemplary embodiment using the screw pump 34 which is excellent. This washout time will ensure against thrombosis by completely washing out the bearing and screw pump surfaces with fresh blood.

Section H—Bearing Hemodynamic Compatibility and Reliability

Why The Journal Bearing Will Not Damage Blood

1. General Comments

The hydrodynamic bearing was designed using as large as practical, a clearance to keep viscous shear stress low in the gap. High shear has been avoided (which also exists in turbulence), since if for a sufficiently long duration, can rupture red blood cells. The body naturally replenishes damaged red blood cells at its own rate, so an acceptably low rate of hemolysis, as exists in all blood pumps, is acceptable. It is the purpose of this section to show that the piston bearing design will not damage blood. First, it will be shown that the magnitude of shear rate in the bearing gap and its duration is lower than the threshold value for blood cell damage. The calculated shear is also much lower than what has been experimentally measured in one of the best presently developed blood pumps, the Penn State LVAD. (Ref. "Hot film Wall Shear Probe Measurements Inside a Ventricular Assist Device", by J. T. Baldwin et. al, Journal of Biomedical Engineering, Vol, 110, November 1988, pp 326–333). Consequently, little if any damage should occur in the proposed design. Thirdly, this conclusion will be fully supported by submitting experimental hemolysis data taken on a rigid-vane, artificial heart pump that used a similar gap as a clearance seal for the oscillating vane. Blood was not damaged in the gap because the threshold value for shear damage was not exceeded. The pumps hemolysis index was lower than, or at worse the same as, the best rubber ventricle pumps tested. Fourthly, the hemolysis index (HI) of the proposed design is calculated; assuming that all or 100% of the blood flowing through the bearing becomes damaged. The result is still an HI lower than that of existing blood pumps.

The data presented in this section is intended to prove beyond a reasonable doubt that the hemolysis index of the proposed design will not be worse than conventional rubber ventricle designs. On the contrary, one concludes from the available pool of knowledge that it should be superior.

Hemolysis of blood normally occurs in heart valve wakes and other highly turbulent areas within a pump, primarily on foreign surfaces. Most conventional pumps use elastomeric ventricles that squeeze the ventricle in one direction and blood flow occurs in an orthogonal direction. This direction change can create extremely high shear rates as well as high acceleration body forces on the red cells which increases their chance of rupture. Extremely high blood shear was experimentally measured in the Penn State Pump by J. T. Baldwin et al, and will be compared to the proposed bearing. This undesirability does not occur in the proposed pump because blood flows unidirectionally through it. Its straight-through flow design is ideally suited to minimizing shear and turbulence in the pump. IBM will be using its computing facilities to analyze the flow through the pump; tracking each red blood cell. Turbulence and shear can be minimized by determining optimal internal contours. Good wash out of all areas can be verified by determining points of stagnation.

The rotating bearing with integral valve will create a slow-swirling motion beyond the valve. This washes out the pump exiting surfaces outlet connection, and conduit that attach it to the descending aorta. This same swirling or vortex motion has recently been observed at the exit of the natural heart's aortic valve by researchers at Union College, Schenectady, N.Y. In addition, the vortex flow washes out the entrance to the aorta eliminating areas of regurgitation and stagnation behind the aortic valve. This gentle action resulting from piston rotation can only be desirable in the pump.

The continual linear motion and rotation of the bearing provides similar low shear stress cleansing of the gap enhanced by continuous washout with fresh blood by the screw viscosity pump. Even with all of this activity going on in the bearing gap, let us now show that the flow remains smooth and laminar. In other words, turbulent flow does not occur. This will validate the velocity distribution calculations in the gap, the calculations of shear stresses at the bearing surfaces, and will validate the load capacity calculations in the section on bearing design, where flow is assumed laminar.

Laminar flow is maintained provided the Reynolds number in the gap 30 is below approximately 2,300. This number is the ratio of inertial forces to viscous forces.

Analysis predicts that flow is laminar by a wide margin, and all of the calculations are validated. Moreover, highly laminar flow in the gap by three orders of magnitude, excludes the possibility of turbulence, particularly on polished surfaces.

2. Determination of Blood Shear In Bearing Gap

The linear motion of the piston results in fluid shear in the bearing gap because one surface (the piston) is moving at velocity Uo and the housing is stationary. The bearing also has an external pressure P imposed during systole which produces an additional parabolic velocity profile.

Figure 25:
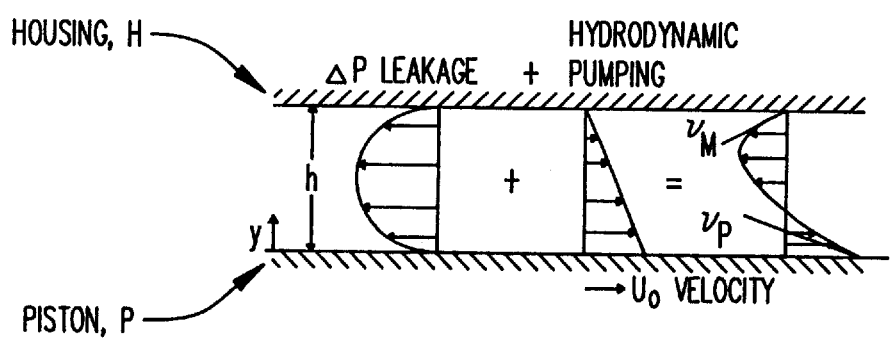
FIG. 25 is a schematic representation of velocity distribution in the gap between the piston and housing of the linear pump illustrated in FIG. 2.

The physical interpretation of blood shear is shown in FIG. 25 where the two velocity distributions are additive in the gap. (Note: Shear is a maximum on each surface not within the gap.) These flows being additive, result in the net velocity profile shown at the right. Blood shear v at each surface is the slope of the velocity profile at the respective points as shown.

$v = du(\text{shear rate-sec}^{-1})/dy$

Figure 26:
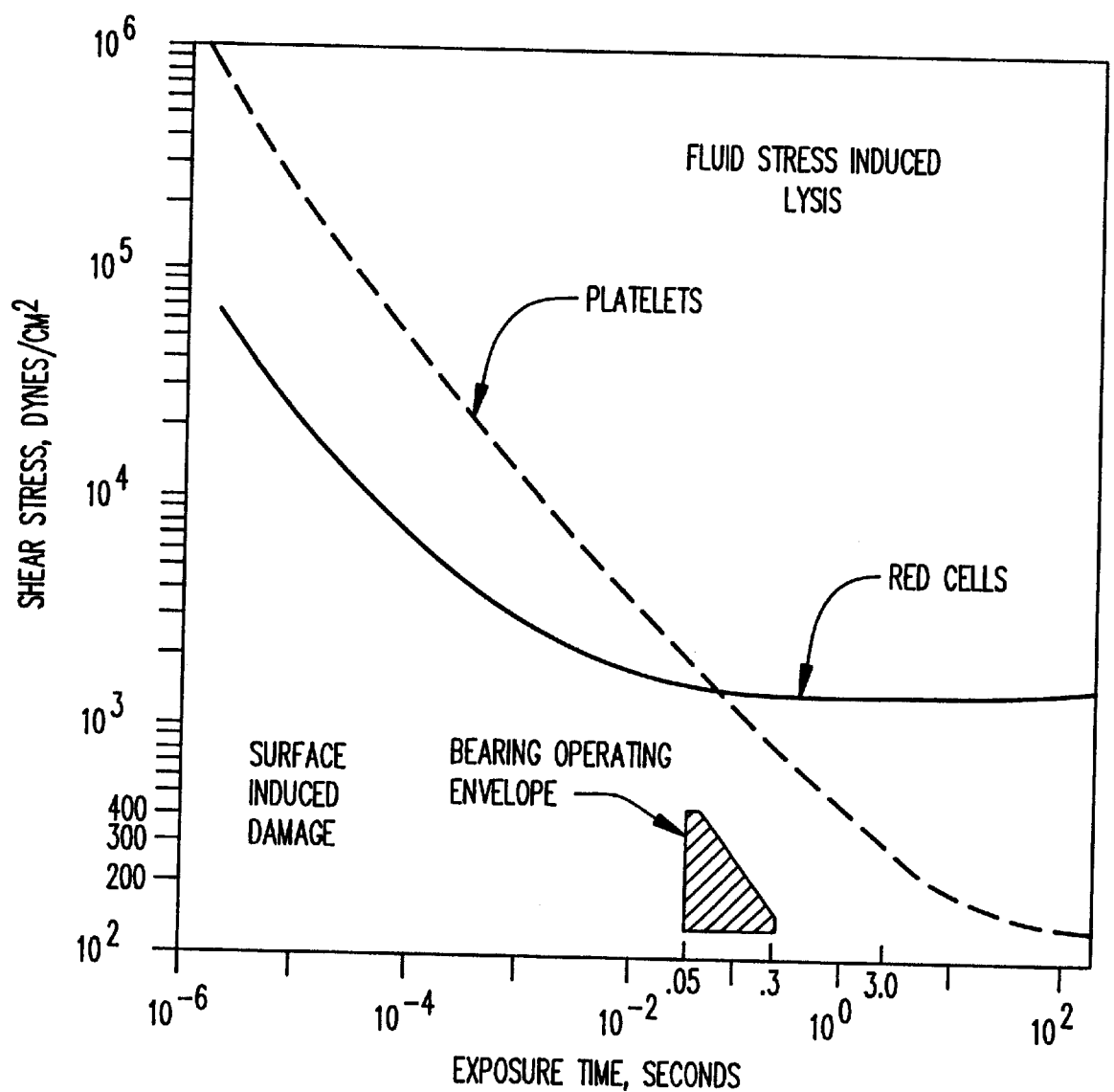
FIG. 26 is a graph plotting acceptable shear stress versus time duration for blood components.

Shear stress=($\mu$×shear rate) dynes/cm$^2$ $\mu$=blood viscosity 28.6 dynes sec/cm$^2$ It is now generally accepted that the amount of blood cell shear damage is a function of both the shear rate u and its duration. This data was published by NIH in 1985, as publication No. 85-2185 entitled "Guidelines For Blood-Material Interactions", a report of the NHLBI Working Group. Blood damage experimental results were presented in the form of curves plotting acceptable shear stress versus time duration. This curve is shown in FIG. 26 and is described as "The locus in the stress exposure-time plane of shear-related damage to blood cellular elements. Regions above and to the right of each line (high stress-long exposure time) would generate significant cell lysis for the given cell type. The curve for PMN leukocytes terminates at one second exposure time because the very short time experiments have not been done as yet. Modified from reference 44."

As can be seen there is a threshold value of shear, below which no red blood cell damage occurs. This threshold value is about 42,900 sec−1 which corresponds to a shear stress of 1,500 dynes/cm$^2$. Trauma to leukocytes can begin at about 300 dynes/cm$^2$ (8,600 sec−1) depending on duration.

Table 4 in Section H-3 which follows presents analytically determined shear stress in the bearing gap and duration for an exemplary embodiment.

3. Meeting NIH Publication No. 85-2185 Design Criteria For Eliminating Blood Cell Damage Shear rate v values exist at the wall surfaces only and are zero at some point in the middle of the gap. Hence the percentage of gap blood volume that experiences these rates is small. Induced shear stresses of low magnitude on foreign surfaces is highly desirable for good wash out. (Ref. Dintenfass, L. and Rosenberg, The Influence of the Velocity Gradient on in-vitro Blood Coagulation and Artificial Thrombosis, J. Atherosclerosis Res., " Vol. 5, pp. 276–290, 1965.)

Table 4 shows shear stress and the duration over which it acts during systole and diastole. These coordinates can now be located on the blood damage lysis graph of NIH Publication No. 85-2185 to determine if any blood damage can occur.

FIG. 26 also includes a shaded box showing where the pump's operating envelope lies taken from points plotted from table 4. Exposure times vary (for systole and diastole) from 0.050 to 0.282 seconds respectively and shear stress varies from 130 to 460 dynes/cm². The piston decelerates and stops separating systole and diastole times allowing the blood cells in the gap to relax. As can be seen, the shaded box is well beneath the lysis curves for both red cells and platelets, so little if any damage will occur. The degree of safety factor is rather substantial.

It may not be desirable to have too low a shear rate in the bearing gap in order to properly wash out its surfaces. The linear bearing motion coupled with the rotary motion and screw pump flow is helpful in washing out the gap and minimizing the tendency to cause thromboli. Page 77 of the NIH document, "Favorable Conditions", states: "Ideal conditions for circulation in an artificial organ are those in which cell activity or destructive forces are minimized, yet blood flow is maintained. Hemodilution reduces both blood hematocrit and plasma protein levels. This effectively reduces cell collision frequency and red cell aggregation. Shear rate, optimally, should be high enough to provide disaggregating forces for weak aggregates and remove weekly adherent cells from a wall, yet not so high as to cause appreciable hemolysis or significant sublytic damage to blood or endothelical cells." The linear motion induced shear during both systole and diastole portions of the cycle induce a low shear stress value of 130 at 3 L/m which goes up to 460 at 10 L/m as shown in the previous table. The bearing motion and pump wash out thus guarantees "dilution" and a level of at least 130 dynes/cm² provides "disaggregating forces." Yet the highest shear level of 460 is far below any threshold for damage (by at least a factor of 5).

There is only one last shear stress-time-factor to consider and that is the shear stress induced by the 72 RPM rotation of the bearing. As noted at the beginning of these calculations, the surface velocity from rotation is 5.8 in/sec. Using this value, the gap shear rate is computed to be 3,860 sec⁻¹ which is a shear stress of only 135 dynes/cm². Referring once again to the NIH lysis plot in FIG. 26. we see that this point falls way below the red cell curve for time equals infinity, the critical value being about 2,000 dynes/cm². As far as platelets are concerned, we know that the screw pump flow (see Section I) flushes the bearing out with fresh blood in 3 seconds. At the 3 second abscissa, one reads off a critical shear stress value of 350 dynes/cm².

The rotary motion induced shear stress of 135 dynes/cm² is 250% below this threshold value, so little or no platelet damage is expected as well.

Conclusion: There is every scientific foundation to believe that the journal bearing will operate long term as planned, without inducing appreciable hemolysis or platelet damage. The danger of emboli is also minimized by inducing low and desirable shear stresses on the bearing surfaces which being polished Biolite carbon are already resistant to thrombosis. Reliable wash out of the bearing gap by screw pump forced flow (which must doubly serve to make up bearing end leakage) insures reliable "dilution" with a continuous resupply of fresh blood, long recognized as being essential.

Section I—Piston Linear Bearing For LVAD

As an alternative to creating a supporting film of blood for the piston by virtue of its rotation, one can support the piston both radially and torsionally using a linear hydrodynamic blood bearing. A similar linear support bearing is disclosed in U.S. Pat. No. 5,360,445 but used oil as the fluid. When using blood, additional design constraints are required such as use of acceptable shear rates and durations as well as flush out of the bearing clearances. These constraints can be met using the hydrodynamic pumping effect to wash out the bearing. This hydrodynamic pumping effect eliminates the need for a screw pump to supply pressure to the bearing.

The linear motion of the piston creates its own axial pressure distribution in the bearing. With the piston displaced off center radially, an unequal circumferential pressure distribution results to give a net support pressure radially. By providing at least two axial pressure building pads 42a an axial distance apart, tilt stiffness is produced as well. The bearing geometries illustrated in FIGS. 27 and 28 were investigated in detail and are acceptable blood bearings for an LVAD piston. FIG. 27 illustrates schematically a double-acting or two-directional bearing steps or pads 42a arrangement. FIG. 28 illustrates schematically a single-acting or one-directional bearing steps or pads 42b which support pressure when the piston moves to the left only in the reset stroke. Both embodiments have transient squeeze film load capacity.

The gaps $h_o$ and $h_1$ are on the order of 0.001" respectively. The ratio of $h_1/h_o$ can be optimized to give the maximum radial load capacity for an entire range of radial displacements of the piston. The sharp edges of the steps in reality would be rounded or blended in at an approximate 10 degree angle to avoid flow separation and turbulence.

The above linear bearings need to be conservatively designed as far as load capacity is concerned using the minimum expected blood viscosity. Load capacity for a given speed depends on blood viscosity and viscosity can vary with the health of the patient. A big advantage of the rotary journal bearing discussed in the above referenced disclosure is that load capacity is independent of viscosity if a constant average torque is applied to the piston. This advantage markedly helps in initial implantation where saline of low viscosity is employed.

Figure 29:
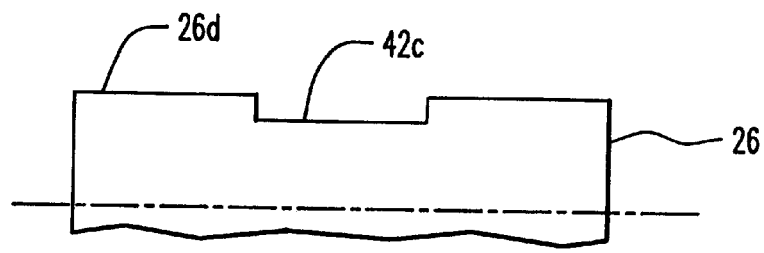
FIG. 29 is a schematic representation of a journal bearing formed in the gap between the piston and housing of the linear pump illustrated in FIG. 2 for supporting the piston therein in accordance with an exemplary embodiment of the present invention.

To reduce the outlet pressure required of the screw viscosity pump 34 in the journal bearing adaptation to flush out the gap and to eliminate the formation of cavitation within the bearing, a central step 42c may be provided to effectively decrease the washout length. This is shown in FIG. 29. However, load capacity of a central step bearing is less than that of a non-step bearing.

This central gap 42c does not produce any net axial bearing effect. However, using bearing geometries in FIGS. 27 or 28 does produce a linear axial bearing effect even though the piston 26 is rotated. The step heights $h_1$, effectively reduce the length of the piston so that less screw pump pressure is required and a shorter screw pump can be utilized. If the linear bearing configuration is employed together with rotation, then a screw pump 34 is still desirable.

The pump 34 shown in FIG. 30, is ideally located at one end of the piston 26 adjacent to its high outlet pressure during the cycle (systolic pressure). In this way systolic pressure flow through the bearing will be in the same direction as the screw pump flowrate for added effect. This holds true for the double-acting bearing geometry 42a where there is no net flow through the bearing from axial motion even though the velocities may be different in each direction.

On the single-acting bearing 42b, gap flow from axial motion is from right to left relative to the piston which is moving to the right. The screw pump 34 would then be positioned on the right side of the bearing to add to this flow. Ideally, systolic pressure would be on the right side to add to this flow.

FIGS. 30—32 illustrated in more particularity the screw pump 34 which provides means disposed at the journal bearing gap 30 for pumping a portion of the blood 12 from the housing bore 22a into the piston gap 30 for accommodating or making-up leakage from the gap 30 at the opposite ends of the piston 26. The screw pump 34 includes a plurality of circumferentially spaced apart screw threads 34a having respective screw grooves 34b therebetween for channeling the blood therethrough. The screw pump 34 preferably also includes an annular groove defining a manifold 34c disposed in flow communication with the screw grooves 34b for collecting the blood therefrom to uniformly distribute the blood circumferentially around the piston gap 30 then over the piston journal or surface 26d. In the preferred embodiment, the piston gap 30 includes a bearing portion 30a at the housing inlet end, and a pump portion 30b at the housing outlet end. The pump gap 30b is preferably smaller than the bearing gap 30a to reduce screw pump leakage from the manifold 34c.

As the piston 26 is caused to spin in a right-hand type screw fashion as illustrated in FIG. 30, the screw threads 34a channel and pump the blood 12 into the manifold 34c disposed at a suitable position between the opposite ends of the piston 26. Since the pump 10 will assume different orientations relative to gravity depending upon the orientation of the person in which the pump is implanted, the manifold 34c ensures that uniform blood pressure is provided around the entire circumference of the piston 26 irrespective of its orientation with respect to gravity. And, the pressure of the blood within the manifold 34c enjoys the benefit of the combined pumping effects of the individual screw threads 34a which discharge into the manifold 34c.

Although the screw pump 34 may be formed in either the inner circumference of the housing 22 or the outer circumference of the piston 26, in the preferred embodiment illustrated in FIG. 30 the screw pump 34 is formed in a portion of the outer surface defining the piston journal 26d, and is disposed adjacent to the piston outlet 26c for working in concert with axial translation of the piston 26.

As shown in FIG. 31, each of the screw grooves 34b includes an inlet 34d disposed at the aft end of the piston 26 for receiving the blood 12 from the housing bore 22a.

The screw pump 34 is preferably located at one end of the piston 26 in order to reduce interference with the load carrying remainder of the piston journal 26d, and to unidirectionally purge out the bearings from one end with fresh blood. The groove manifold 34c uniformly delivers pump pressure all around the circumference of the bearing. This allows the make-up flow to enter the bearing at any angular orientation around the bearing. The screw pump 34 forces blood into the bearing under pressure, and therefore fluid pressure does not go negative, and blood cell damage from negative pressure conditions is eliminated.

The screw pump flowrate is proportional to the spinning speed of the piston 26, and bearing end leakage is also proportional thereto. Accordingly, the pump will automatically pump more as speed increases. The screw pump therefore automatically compensates for speed changes. In the case of a constant torque being applied to the piston 26, the piston will speed up if viscosity decreases. The additional speed pumps more fluid, and bearing flowrate will compensate for viscosity changes as well.

The screw pump 34 therefore provides self bearing pressurization due to rotation of the piston 26 to accommodate bearing end leakage. And, the screw pump 34 washes out the piston gap 30 with fresh blood and aids in heat transfer cooling.

Analysis indicates that the optimum number of screw threads is about four for this design configuration utilizing one complete turn of 360°. Therefore, only four one-turn screw threads 34a and grooves 34b are used in the preferred embodiment and are equiangularly circumferentially spaced apart from each other.

In a preferred embodiment, the screw threads 34a have a helix angle of about 11°, with the depth $D_g$ of the screw grooves 34b as shown in FIG. 32 being about 5 mils for example. The lateral width $W_g$ of each screw groove 34b is about 125 mils in the preferred embodiment. The manifold 34c is about 60 mils wide and 8 mils deep for example.

As shown in FIG. 32, the screw threads 34a are defined by sidewalls 34e extending radially inwardly from the journal 26d which defines a smooth land, to respective groove bottoms 34f. The sidewalls 34e are preferably inclined or tapered axially adjacent to the journal lands 26d for minimizing flow separation of the blood as it flows into and out of each of the screw grooves 34b. This flow is primarily from axial translation of the piston 26, and partially from blood pressure in the manifold 34c. The taper of the sidewalls 34e near the journal 26d is less than about 10° to eliminate flow separation, and is about 7° in a preferred embodiment for limiting acceleration and deceleration of the blood flow out of and into the screw grooves 34b and over the screw threads 34a for minimizing the possibility of blood damage.

In an exemplary embodiment, the sidewall taper extends over a taper width $W_t$ of about 10 mils which is about twice as large as the radial depth $D_g$ of the screw grooves 34b, which is about 5 mils. With this exemplary embodiment, fresh blood replenishes the piston gap 30 about every three seconds or 18 pump cycles.

Section J—LVAD Control System

Introduction

Figure 33:
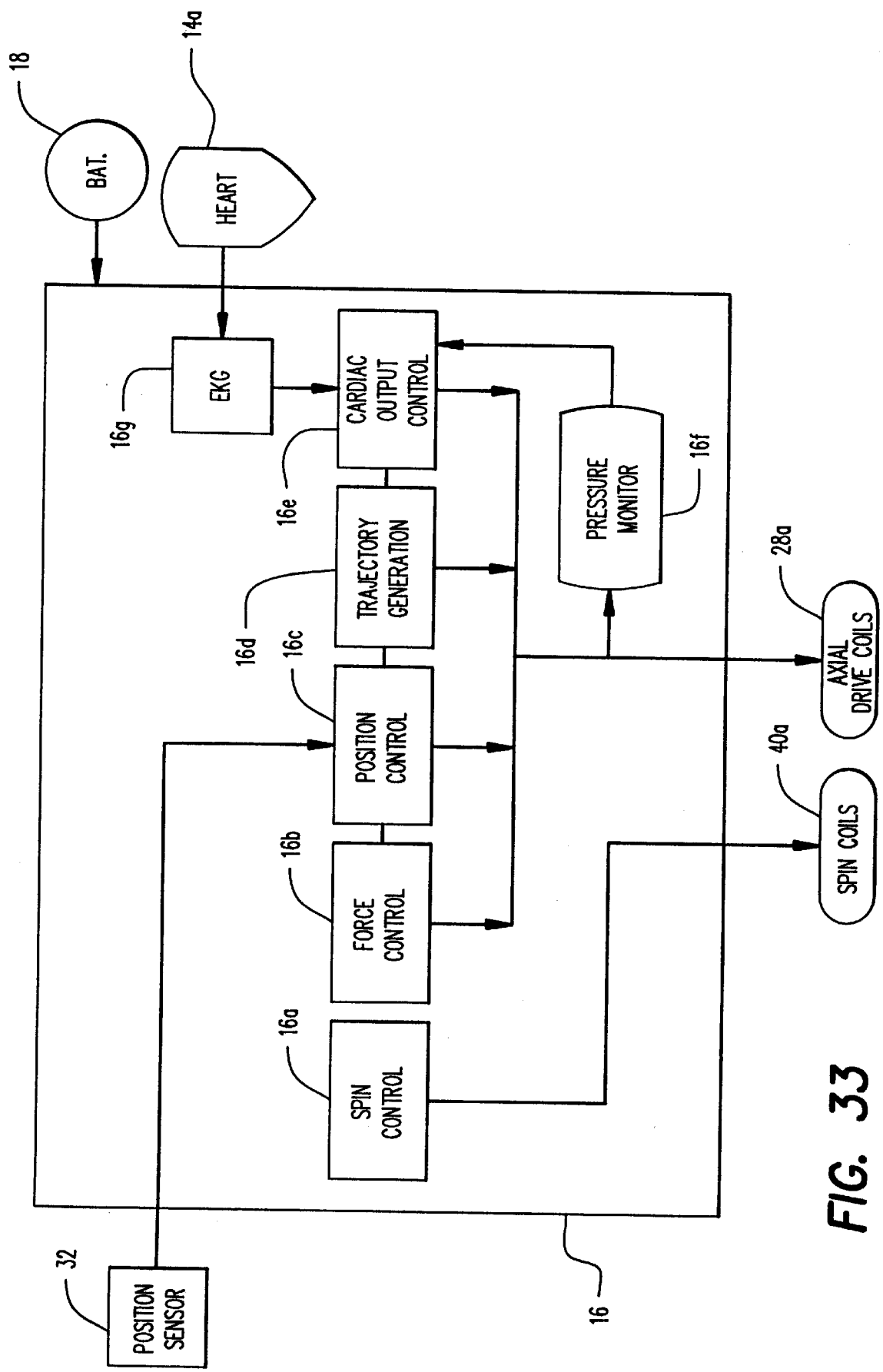
FIG. 33 is a schematic representation of a controller for controlling operation of the fluid pump illustrated in FIG. 2 in accordance with an exemplary embodiment.

The electronic controls found in the controller 16 for the reciprocating, electromechanical direct-drive LVAD pump 10 includes 5 elements or modules for, as shown in FIG. 33,: spin control 16a, current (force) control 16b, position control 16c, trajectory generation 16d, and cardiac output control 16e. Four of these five layers may be executed by a single microprocessor, and the fifth by a separate microprocessor. Such organization permits decomposing the process into simple modular functions, each of which can invoke existing proven techniques, and each of which can be debugged and revised more simply than a single, more complex process. All control code may be written in a portable language ("C" or "C++" for example). Unlike assembly language programs commonly used in the past, use of a higher-level, portable language permits application of the same source code to a variety of disparate microprocessor architectures, including future microprocessor designs.

a. Spin Control

The purpose of the spin module 16a is to induce a continuous spin on the pump piston 26. Such spin provides the supporting pressure generated in the bearing for maintaining a film of blood in the fluid gap 30 of the hydrodynamic bearing. (This bearing pump flow should not be confused with the cardiac output, which is orders of magnitude larger). While the flowrate required to maintain the fluid film is tiny, it is nonetheless important, so as to prevent wear due to rubbing contact between the piston 26 and housing 22. The bearing is designed such that a continuous rotation of approximately 72 RPM of the piston 26 will provide the necessary bearing-pump action. It should be noted that, if the viscosity of the blood were to lower, greater fluid pumping to the hydrodynamic bearings automatically takes place via increased rotation rate of the piston.

In one simple implementation, spin control of the piston 26 may be effected by a pure current source to the spin coil 36b or 40a. Given a constant current, a constant torque would be induced on the piston. At constant torque, the piston rotation rate in steady state would balance the viscous drag of the blood film. If the blood viscosity were to change, the corresponding piston rotation rate would change as well (inversely proportional). This effect is a natural feedback, providing the spin compensation required. For example, when increased film pumping is required for lower viscosity blood, the lower viscosity would lead to a higher spin rate, thus yielding the required increased pumping rate. It is not necessary that the spin rate of the piston be regulated. Thus, this natural feedback will be adequate to maintain the necessary fluid film in the hydrodynamic bearing. This is discussed in detail in Section G.

The number of turns of the spin coil 40a are chosen such that the driver need only supply a mere 0.14 Amps continuous for a nominal power consumption of 58 mW. This current would be supplied from the batteries 18 via a Pulse-Width Modulated (PWM) circuit with inductive current smoothing and current feedback. Such switching circuitry is now standard practice, as PWM designs offer small packaging, high reliability and high efficiency. Given the natural viscosity-compensating feedback inherent in a pure current-source control design, it will not be necessary to compose any microprocessor code for spin control. The electronics for this function can be completely isolated from the cardiac output controller 16e.

b. Piston Force Control

At the innermost level of cardiac output control, it will be necessary to regulate the piston thrust on demand. For the radially-magnetized piston, electromagnetic force is, ideally, proportional to the coil current. Improved efficiency is provided by the three separate drive coils 28a for selective activation over the stroke of the piston 26. With this variation, only "active" coil turns are driven, thus providing full output force at reduced coil resistive losses. To exploit this advantage, though, it is necessary to intelligently select which coils should be driven at any instant. While this approach may seem complex, it is, in fact, common practice in motor control. All brushless D.C. motors exploit this technique in rotary form, exciting (electronically commutating) one of three coils as a function of detected rotor angle. This scheme is also employed in less common, but commercially available 3-phase linear induction motors.

The present implementation will mimic proven industrial practice. Selection of the active coils at any instance (each control sample) would be indexed according to the sensed position of the piston. Current control of the selected drive coil (or coils) 28a may be performed by a PWM power amplifier with analog current feedback, and inductive current smoothing. PWM amplifiers are selected for the same reasons as the spin driver: high efficiency, high reliability, and compactness. Proportioning of current in the active coils results in 33% less power consumption, as discussed in Section C.

c. Trajectory Tracking Control (abbreviation legend: des=desired; sns=sensed; cmd=command; sys=systole; dias=diastole)

Given the existence of a function which exerts piston forces on command, trajectory tracking control in the position module 16c is quite simple. A standard Proportional-plus-derivative (P-D) Proportional Derivative control loop may be employed, with the form:

$$F_{cmd}=k_p(X_{des}-X_{sns})+K_v(v_{des}-v_{sns})+ma_{des}.$$

Here, $F_{cmd}$ is the value which would be passed to the underlying force module. $F_{cmd}$ is computed based on a desired position, $X_{des}$ and velocity, $v_{des}$, relative to the actual sensed position and velocity, $X_{sns}$ and $v_{sns}$, respectively. For rapid acceleration conditions, the feed forward term in desired acceleration, adeS, further improves tracking, though this term is an optional refinement. The position gain $K_p$ and velocity gain $K_v$ provide the necessary feedback to enforce that the piston track the desired position and velocity commands. In practice, the "sensed" velocity would actually be inferred from numerical differentiation of successive position readings. Positions, $x_{sns}$, would be read from the piston displacement sensor. The entire control loop would repeat its computation of $F_{cmd}$ at a rate of approximately 1 kHz. Such control is easy to compose, and is standard practice in proven equipment, such as computer peripherals, robots and machine tools. Construction of this layer, though, assumes the existence of a trajectory command, ($x_{des}$, $v_{des}$ and $a_{des}$), which must be generated at a higher level, as described next.

d. Trajectory Command Generation

Figure 34:
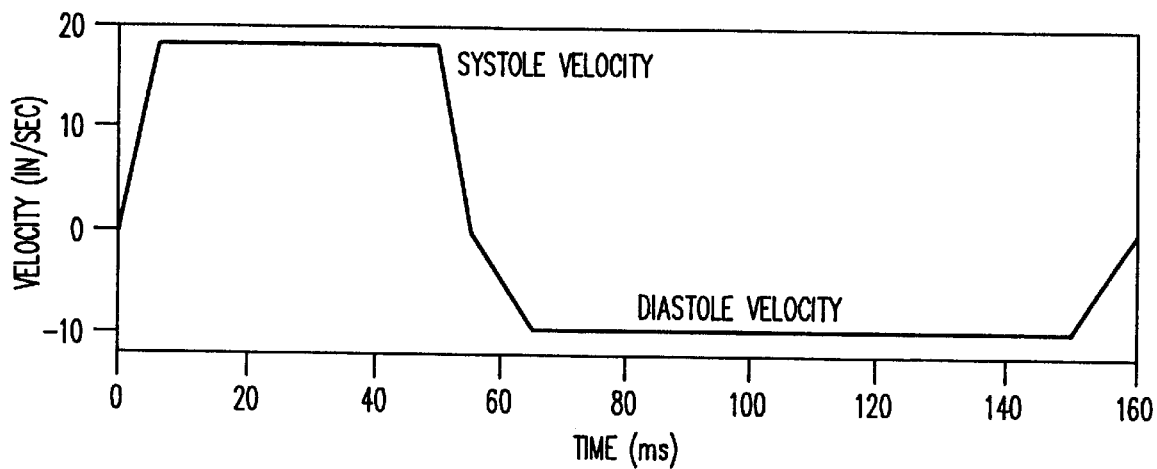
FIG. 34 is an exemplary graph plotting piston velocity as a function of time for one cycle of the piston shown in FIG. 2.
Figure 35:
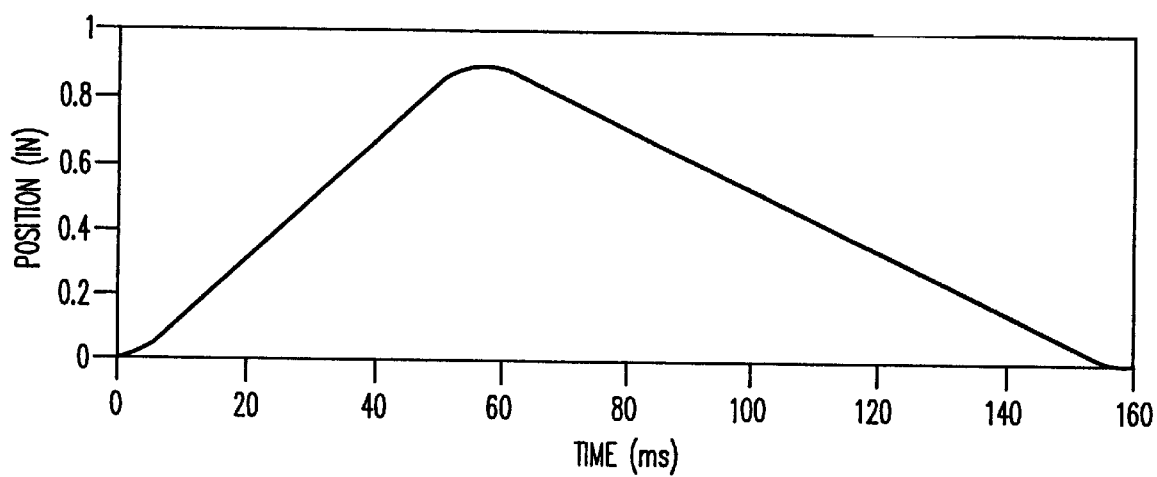
FIG. 35 is an exemplary graph plotting piston position versus time for the corresponding cycle illustrated in FIG. 34.

Specification of $x_{des}$, $v_{des}$ and $a_{des}$ to the lower-level trajectory tracking controller is a simple algebraic computation in the trajectory module 16d. It can be performed at update rates in excess of 1 kHz as one of several tasks running on a single, inexpensive microprocessor. The particular trajectory chosen for piston control is optimized for pump efficiency. This trajectory is shown in FIGS. 34 and 35. FIG. 34 illustrates piston velocity and FIG. 35 illustrates piston position during a complete cycle from eject to reset strokes. The generic shape of the trajectory is known as a "trapezoidal velocity profile"—a waveform which is ubiquitous in the field of machine control due to its desirable dynamic properties and ease of computing. In FIGS. 34 and 35, the waveform is illustrated beginning from the zero-velocity point at the extreme left (atrial) side of the pump. The desired trajectory then ramps up the velocity at a constant rate (constant acceleration) for duration $T_1$, until it reaches peak velocity $v_{sys, peak}$. The desired acceleration, $a_{des}$, during this period is $v_{sys, peak}/T_1$. When the piston reaches the target peak velocity, the motor efficiency is optimal. The piston then continues to move at constant velocity for time $T_2$. Near the end of the stroke, the piston will decelerate over time $T_3$ to zero velocity as it reaches the stroke limit. The return stroke (diastole) follows a similar profile, accelerating to (negative) velocity $v_{dias, peak}$ over time T, continuing at negative velocity $v_{dias, peak}$ for duration $T_5$, and finally decelerating over time $T_6$ to zero velocity as the piston returns to the starting (left, or atrial) position.

For each segment of the trajectory, the position and velocity commands follow as simple functions of the chosen time constants, $T_1$ through $T_6$, and the chosen peak velocities. These time constants cannot be chosen arbitrarily, though, as there is an integral constraint corresponding to the net displacement. In our preferred solution, $v_{sys,peak}$ is set to the velocity of peak motor efficiency, 18"/sec. Further, the acceleration and deceleration times are chosen to consume only 20% of the systolic stroke time. As a result, we select $T_1$=5.5 ms, $T_2$=44 ms, and $T_3$=5.5 ms. To match the velocity constraint, the slope of the trapezoidal velocity profile (i.e., the acceleration) is approximately 3,300 in/sec². With these parameters, nearly 90% of the systolic stroke is performed at the peak-efficiency velocity.

Since the return stroke requires only minimal power, it is not important to optimize its return velocity. Thus, the times $T_4$, $T_5$ and $T_6$ can be varied to allow for a variable beat rate of the pump. For example, given 55 ms for the pump stroke and 105 ms for the return, the resulting beat rate would be 6.25 Hz, or 375 beats per minute. Given a net expulsion of 16 ml per stroke (which accounts for the computed backflow), the corresponding cardiac output would be 6 liters per minute. If the return time were to speed up to match the systolic stroke time of 55 ms, the corresponding beat rate would increase to 545 beats per minute, with a net cardiac output of 8.7 l/min. Nearly 10 l/min can be achieved with this design by increasing the beat rate further, up to 600 beats per minute. The larger pump requires lower beats per minute.

In short, the trajectory generator level invokes the algebraic rules for each of the six trajectory segments, subject to the velocity and stroke length constraints. The result is continuous recomputation of $x_{des}$, $v_{des}$ and $a_{des}$, which are passed down to the underlying trajectory tracking controller as trajectory commands.

Determination of $T_1$ through $T_6$ requires the additional specification of desired net cardiac output. This specification comes from the final, highest level, described next.

e. Physiological Control Options

The highest control level consists of the cardiac output regulator or module 16e. This level specifies the desired net flowrate, or, equivalently, the desired pump beat rate. Given such specification, the lower control levels are capable of performing all the actions required to achieve the target output.

Regulation of cardiac output should depend on physiological demands. Determination of the physiological demand must be performed indirectly. Below, four viable methods are described.

1. Natural Pacemaker Control

If the patient's regulatory system is functioning properly, then target flowrate could be specified as a fixed ratio between the natural pacemaker signal and the LVAD beat rate. The natural beat rate could be measured using a suitable EKG monitor 16g to detect the natural heart's EKG signal. In this mode, the LVAD would automatically speed up in response to the natural heart rate. As all of the body's feedback systems would be operative, physiological demand would be met appropriately.

Since the stroke volume of the LVAD is about ¼ that of the natural heart, nominally 4 pump cycles would be used for every heart beat of the natural heart. One pump size would be able to span the flow requirements of different size adults. For large individuals a ratio of slightly more than 4 to 1 would be employed. For smaller individuals a ratio of proportionately less than 4 to 1 would be used. This ratio, called the Heart Synchronization Ratio HSR, should be tuned to the size of the recipient.

This can be accomplished without violating the hermeticity of the electronics package which will be sealed in a titanium module. A simple digital telemetry link to the microprocessor controller may be used (not shown). The HSR can be digitally stepped up or down in small increments until the desired diastolic pressure is reached. The diastolic pressure can be verified using a standard blood pressure arm cuff at the time of implantation. The same pressure information is available directly from the pump over its telemetry link. This provides a simple means to adjust average blood pressure if need be, over the life of the patient; whether to compensate for arteriosclerotic build-up or other factors.

In many instances, however, patients in need of an LVAD may not be producing appropriate, dependable pacemaker signals. In such cases, alternative means for regulating cardiac output must be employed. Three such options are described below.

2. Inferred Demand from Pump Work

Piston Use as Systolic Pressure Transducer—The force produced by the linear motor 28 is directly proportional to motor current. Since the force on the piston, when it is not accelerating, is directly proportional to the differential pressure across the piston, differential pressure will be directly proportional to current. The piston rides virtually friction-free on its hydrodynamic bearing so friction does not exist to detract from the accuracy obtainable using the piston as a transducer.

Aortic pressure is typically 120 mmHg while pump filling pressure is much smaller. Hence, the measured differential pressure is very nearly pump output pressure. A constant correction factor for pump filling pressure can be used to obtain a corrected, more accurate, value of output pressure if desired. However, once a set point is established for the physiological controller, this may not be necessary.

Piston differential pressure is independent of environmental pressure changes. Body blood pressure varies directly with changes in environmental pressure and this equally effects blood inlet and outlet pressures at the pump. In other words, the piston is a gauge differential pressure transducer and does not respond to absolute pressure. This is just what we want, so that monitoring of environmental pressure is not required and the LVAD can be hermetically sealed.

Motor current provides an instantaneous or real time aortic pressure signal. This is used with the following two physiological control options, namely, cycle work done or maintenance of average systolic pressure.

One simple control option is to infer flow requirements from the work performed by the LVAD per stroke. Since the piston velocity will be regulated, the work performed will be proportional to the current exerted by the tracking controller. The piston acts as an integrated pressure transducer where current is proportional to systolic or aorta pressure. When the work per beat decreases, the body's peripheral resistance has lowered, which is a physiological response to the need for more flowrate. When lower work per beat is detected, the beat rate should be increased until the target work per beat is reached (subject to minimum and maximum flowrates). The beat frequency, f, would be adjusted per:

$$f_{i+1} = f_i [1 + a(W_{nominal} - W_{actual})/W_{nominal}].$$

Using this scheme, the beat frequency command at iteration i+1, $f_i+1$ would be adjusted relative to the previous beat rate, $f_i$, proportional to the target work-per-beat, $W_{nominal}$, and the measured actual work per beat, $W_{actual}$. The constant "a" tunes the speed of response, which can be adjusted to emulate a natural response. Work per cycle is obtained as the integrated value of motor current times displacement. This method does not depend on changes in altitude or other influences on ambient pressure. As a result of the above approach, the average aortic pressure would be controlled to be roughly constant. Note, though, this controller requires no additional pressure sensor. Rather, since piston friction is negligible, motor current (which is proportional to piston force) is proportional to the pressure.

The controller 16 therefore further includes means 16f in the form of a suitable electrical circuit for monitoring electrical current to the drive coils 28a for determining differential pressure across the piston 26, which is thereby used for controlling differential pressure in the pump 10.

3. Differential Pressure Regulation

Under an alternative approach, the beat rate may be adjusted to regulate the average aortic vs atrial pressure, as sensed by pressure transducers (not shown). The pressure rise from the filling pressure to the expulsion pressure should be approximately 120 mmHg. If the pressure drop falls below the target pressure, $P_{nominal}$, then the beat rate should be adjusted upwards to provide greater flow, and vice versa. The algorithm for adjusting beat frequency can be expressed as:

$$f_{i+1}=f_i[1+a(P_{nominal}-P_{actual})/P_{nominal}].$$

This formula is virtually identical to the previous method, except that the pressure is sensed directly, rather than inferred from motor work. No advantage in using separate pressure sensors is apparent since they would be intrusive, have drift concerns and require additional electronics. Since the motor current already exists as a reliable integrated pressure transducer, this is preferred.

4. Saturation Venous Oxygen Regulation

Finally, a preferred cardiac output control method may be based on direct sensing of oxygen needs. Using a saturation venous oxygen sensor SVO2 sensor) in the right heart, the beat rate can be adjusted to maintain a target blood saturation level. Ordinarily, the blood in the right heart should be 60–65% saturated with oxygen. At higher saturation, the heart should slow down, and at lower saturation, the heart should speed up. If the target oxygen saturation level is $S_{nominal}$, and the sensed oxygen saturation level is $S_{actual}$, the beat frequency can be adjusted according to:

$$f_{i+1}=f_i[1+a(S_{nominal}-S_{actual})/S_{nominal}].$$

While the SVO2 sensor is the most direct measure of cardiac demand, this sensor would require additional development. The fiber optic probe itself is suitable for long term implantation. However, the electronics associated with this probe have never been miniaturized for the purpose of implantation. While this should be feasible, it would require a development effort.

5. Summary of Physiological Control

In each of the control options above, beat rate is adjusted relatively slowly (over tens of seconds) to bring some sensed measure to a target value, whether detected heart rate, work per beat, average aortic pressure, or saturation venous oxygen. Having determined the target beat rate, this frequency is passed as an argument to the underlying trajectory generator 16d, which in turn commands the trajectory tracking controller 16c via the force controller 16b.

Redundancy: The LVAD pump 10 may utilize one microprocessor for pump control as previously outlined, and a separate microprocessor for diagnostics and communications. A third microprocessor may be employed for redundancy of control system functions.

Conclusion: Control of the heart pump 10 can be accomplished using standard techniques used in industry. These include: electronic commutation, PWM amplifier designs, linear trajectory tracking control, and trapezoidal velocity profile generation. Control of desired cardiac output must be based on some physiological indicator. Four candidates are available, including LVAD beat rate adaptation to the EKG signal if reliably available; average pump work per beat; average aortic pressure; and saturation venous oxygen. Each of these signals provide feedback from the body to the LVAD to adjust an appropriate flowrate.

Section K—General Biocompatibility

1. Long-Term Hemo—and Biocompatibility a. Use of Optimum Materials: Biolite Carbon and Titanium

The long-term hemoreliability problems of rubber ventricle use has been eliminated in this design. The all rigid design pump 10 gets rid of this problem. It allows the best use of long-term, proven materials available now and for the foreseeable future. One can do no better to help insure long-term success.

1. Biolite carbon is used throughout the pump 10 for all blood contacting surfaces. This form of carbon is isotropic like pyrolyte and nearly as thrombo-resistant. There is no better material available for long-term hemocompatibility. It is used to coat the titanium suture rings in prosthetic heart valves and provides stable long-term hemocompatibility in this application. There is no reason to believe that it will not function equally well, long term in the LVAD. The Background section presents the advantages of Biolite in more detail.

2. The entire pump is encapsulated in laser welded, hermetically sealed, titanium cans. This is an ideal base material upon which to deposit Biolite. When deposited on titanium, Biolite can withstand 5% elongation without cracking. Small micro-cracks may appear in Biolite coatings when used on flexible polymeric materials. This will not happen on the rigid titanium surfaces of the LVAD, but if it should, the hemoreliability of the coating is not compromised.

Titanium is highly corrosion resistant in blood and will not degrade even if it should become exposed to blood. Titanium also provides the dimensional stability needed for the piston and pump bore surfaces. This was proven in the Phillips Cryo-refrigerator application, whose surfaces sustained pressures in excess of 220 psi. It is mentioned here because dimensionally stable bearing surfaces in the LVAD insure a uniform gap size which maintains the hemodynamic reliability of the bearing.

b. Insuring Optional Hemodynamic Conditions

Using the best available hemocompatible materials, as mentioned above, is a major step toward insuring long-term hemoreliability. The thrombogenic, calcification and other chemical problems long associated with the use of rubber ventricles and other less-than-optimum materials, no longer exist in the present design.

The other side of the equation must now be satisfied to reach the long-term goal: Hemodynamic operating conditions within the pump must be such as not to unduly destroy blood cells and they should be conducive to disaggrevation for minimizing thrombogenesis. Proper hemodynamic performance was one of the most important constraints in the design of the bearing. This is briefly summarized in the following items.

1. Blood shear stresses in the bearing gap 30 may be well below lysis values for red blood cells and platelets, as set forth in the NIH "Guidelines For Blood-Material Interactions" (Publication No. 85-2185). This may be accomplished by using a large journal bearing gap and limiting piston velocity to insure low shear rates.

2. The piston gap 30 is continuously washed out every 3.0 sec with fresh blood using a continuous flow screw-viscosity pump 34. This forced dilution has long been known to be qualitatively desirable. Furthermore, the action of the piston in creating low level shear stresses at the gap boundaries provides desirable disaggrevating forces to eliminate thrombogenesis.

3. The screw pump flow (as well as piston motion) eliminates the possibility of stagnation areas within the bearing.

4. The flowrate of blood through the bearing is so very low that the volume of blood that can be damaged will have little effect on overall pump hemolysis.

Since the best hemocompatible material may be used throughout the pump, i.e. isotropic carbon, and since the bearing will (by all calculations and experimental data) have a very low hemolysis index, the only other factor affecting hemodynamic performance, will be the general hydrodynamic conditions within the pump.

The minimization of excessive turbulence, flow separation, cavitation and excessive shear stresses will be realized to provide long-term hemoreliability. The straight-through flow pattern of the instant pump 10 gives us the opportunity to design one of the best performing pumps 10 yet realized.

Conclusion: Having satisfied that the best available hemocompatible material is being utilized; and that the bearing according to all known criteria should have low hemolysis and thrombogenicity and having shown that straight-through flow in the pump will be no worse and probably much better than in conventional designs; there is little more that can presently be done to promote the long-term hemocompatibility of this design.

2. Hermeticity a. No Fluids Used

The fact that there is no mechanism to lubricate (other than with blood) eliminates the need for all extraneous fluids. None are used in this design, so seal problems are eliminated.

b. No Venting or Compliance Chamber

The action of the piston is really more like that of a displacer piston since the volume of blood within the pump does not change. As the piston pushes blood out, an equal volume is forced in at the inlet. Since pump volume does not change, no compliance chamber or venting is required. So the pump is hermetically sealable without the need for internal compliance.

c. No Extraneous Sensors

The piston 26 is used as a gage pressure transducer for two of the proposed physiological control options. Hence, the use of separate or invasive pressure transducers is eliminated along with the need to somehow monitor ambient pressure changes (using vents or telemetry). The use of the motor as a pressure transducer is a substantial design simplification.

The pulsatile flow of the natural heart produces a superimposed pressure at the pump outlet 22c. This heart pressure can be sensed by the piston 26 through change in electrical current sensed by the monitor 16f. Thus, natural heart beat frequency can be detected by the piston 26 and used instead of the EKG signal for physiological control of the pump 10.

3. Pulsatile Flow Justification a. Very Small Size with High Efficiency

The advantages in using a small 18.8 cc stroke volume (¼ that of an adult heart) are two fold. It results in the size of the pump being small enough (129 cc) to fit in the chest cavity under ideal placement conditions. It also substantially reduces the motor force because a smaller piston diameter could be utilized. This increased motor efficiency to 85%.

The advantages do not stop here, they compound one another due to the synergistic or multifunctional dependence of one component on the other. For example, the high motor efficiency results in a truly small amount of waste heat so very little has to be dissipated in the blood. Blood temperature rise in the bearing gap is minuscule.

The small piston diameter (which is a result of the small stroke volume) allows the use of a long stroke which gives rise to a higher piston velocity which increases motor efficiency further (minimum force over velocity ratio). The higher piston speed gives rise to a very high heat transfer coefficient in the bearing gap which further reduces blood temperature rise. The list goes on and on. Low motor force reduces magnet size which reduces motor side load forces which reduces bearing load capacity requirements. A reduced load capacity allows the use of a large bearing gap which as we have learned insures a low shear stress in the blood and a low shear stress in the blood insures no blood damage in the gap, etc. The net result is the ability to meet all physiological and performance requirements with an overall system efficiency of 65%, which is outstanding.

4. Insensitivity to Environment a. Gravity

No orientation problems exist. The proposed implant location is ideal with the pump inlet slanted near vertical. Thus, the piston's weight is down and aids in producing force against diastolic pressure. Pump efficiency will actually increase 1% more than that calculated because of this effect. A horizontal motor was assumed for the calculations. Likewise, if the recipient becomes inverted, efficiency can be expected to decrease 1%.

The piston bearing operates equally well in all orientations. This was accomplished by using a symmetric 360° bearing with make-up screw pump 34 flow located at one end. This screw pump 34 location preserves symmetry of the bearing.

b. Air Pressure or Altitude

The physiological control system of the LVAD pump 10 will likely rely on using the piston 26 as the aortic pressure sensor. As was discussed in detail in Section B, the sensed aortic pressure is independent of environmental pressure changes because the piston responds to differential gage pressure between its inlet and outlet as atmospheric pressure changes, so does left atrium and aortic pressures.

c. Magnetic and Electric Fields

These fields are effectively eliminated and limited to the stator of the motor 28 by insuring that the permendure is not close to saturation. In the present design, stator permeability is still about 5000, so stray flux prefers to travel through it than through air. If necessary, one can always utilize a thin mu metal can as a liner in the outer titanium housing of the motor.

Operation of the motor and position sensor will be unaffected by R.F. or D.C. electric fields. The magneto resistor position signal is a several volt, digital pulse and is immune to R.F. interference. Furthermore, the sensor is located inside titanium cans which act as an ideal shield.

Tables

Tables referenced in the text above are presented on the following pages.

TABLE 1

Animal Experiment

| Institution | Abiomet/THI[1] | CCF[2]/Nimbus | Penn State/3M[3] | University of Utah |
|---|---|---|---|---|
| Animal | Calves | Calves | Calves | Calves |
| Starting Date | June 1991 | July 1991 | March 1991 | September 1990 |
| No. of Cases (as of May 1994) | 9 | 12 | 23 | 8 |
| Duration | up to 108 days | up tp 120 days | up to 160 days | up to 159 days |
| Cause of Termination | elective sacrifice | mechanical failure | mechanical failure | mechanical failure |

THI[1]: Texas Heart Institute
CCF[2]: Cleveland Clinic Foundation
3M[3]: Sarns, 3M Division

TABLE 2

Summary of 45.7 mm Motor Specifications

| | |
|---|---|
| Stroke | 0.900 in |
| Magnet can, piston OD | 1.275 in |
| Magnet ring, length (each) | 0.450 in |
| Magnet thickness | 0.156 in |
| Piston bore at center | 0.591 in |
| Coil OD | 1.598 in |
| Outer ring thickness at center | 0.084 in |
| Pump OD | 1.800 in |
| Pump length | 3.125 in |
| Pump volume | 129 ml |

Weight Summary

| | |
|---|---|
| 1 valve + piston | 0.365 lb |
| 6 copper coils | 0.545 lb |
| 1 valve + housing | 0.367 lb |
| | 1.277 lb (578 gm) |
| | [LVAD Specific Gravity = 4.5] |

Materials

| | |
|---|---|
| Magnetic materia | Vanadium Permendure |
| Magnets | Neodymium iron boron 33 MGO energy. Two rings, 8 matched segments each, or solid rings radially magnetized. |
| Hermetic cans & housing | Titanium or titanium alloy. |

Energy Conversion Efficiency $$\eta = \frac{1}{1 + 1.05\frac{F}{U}}$$

F = force (lb)
U = velocity (in/sec)

TABLE 3

| Qnet (L/m) | Cycle $\tau$ | Diastole $\tau_d$ | Proposal $\tau_d$ | Dwell |
|---|---|---|---|---|
| 2.51 | .337 (sec) | .013 (sec) | .282 (sec) | .269 (sec) |
| 5.42 | .168 | .025 | .113 | .088 |
| 7.36 | .126 | .033 | .076 | .043 |
| 9.30 | .101 | .040 | .051 | .011 |
| 10.16 | .093 | .043 | .043 | 0.0 |

Formula used to compute $\tau_d$ for providing constant turbine torque on average over a cycle:

$$\tau_d = \frac{4.44 \times 10^{-3}}{\tau + .010}$$

TABLE 4

Shear Stress in Bearing Gap and Duration

| | SYSTOLE | | | DIASTOLE | |
|---|---|---|---|---|---|
| Q (L/m) | $\upsilon$ Avg. | Stress dynes/cm$^2$ | $\Gamma_s$ sec | $\upsilon$ | Stress dynes/cm$^2$ | $\Gamma_d$ (sec) |
| 3 | 11,500 | 400 | .055 | 3,700 | 130 | .282 |
| 6 | 11,500 | 400 | .055 | 7,700 | 260 | .113 |
| 8 | 12,000 | 440 | .050 | 10,000 | 350 | .076 |
| 10 | 12,600 | 440 | .050 | 12,600 | 460 | .051 |

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

For example, the linear motor 28 may take various other forms using one or more axial drive coils, and cooperating one or more magnet rings. It may cooperate with the piston in any suitable manner for magnetically oscillating the piston in the housing for pumping the fluid unidirectionally using the two check valves.

Accordingly, what is desired to be secured by Letters Patent of the United States is the invention as defined and differentiated in the following claims:

I claim:

1. A pump for pumping a fluid comprising:
    a housing having a bore disposed in flow communication between a housing inlet and a housing outlet spaced apart at opposite ends of said housing, and a first check valve fixedly joined thereto for controlling flow of said fluid through said housing bore;
    a piston disposed coaxially in said housing bore for axial translation therein, and having a coaxial bore disposed in flow communication between a piston inlet and a piston outlet axially spaced apart at opposite ends of said piston, and a second check valve fixedly jointed thereto for controlling flow of said fluid through said piston bore; and
    a linear motor including a plurality of axially adjoining drive coils disposed in said housing, and a pair of axially spaced apart magnet rings disposed in said piston and spaced radially inwardly of said drive coils for magnetically cooperating therewith to axially oscillate said piston in said housing for pumping said fluid in turn through said housing and piston inlets and outlets in unidirectional flow through said housing and piston bores.

2. A pump according to claim 1 wherein said piston includes a cylindrical journal spaced radially inwardly of said housing bore to define a bearing therewith having a gap for receiving a portion of said fluid from said housing bore as bearing fluid for hydrodynamically supporting said oscillatory piston in said housing.

3. A pump according to claim 2 further comprising means for spinning said piston for circumferentially developing hydrodynamic pressure in said bearing fluid, with said bearing defining a journal bearing.

4. A pump according to claim 3 wherein said piston spinning means comprise a rotary motor including:
    an annular rotor magnet having a plurality of circumferentially adjoining rotor poles; and
    a stator band having a plurality of circumferentially adjoining spin coils disposed in said housing for magnetically cooperating with said rotor magnet for rotating said piston.

5. A pump according to claim 3 wherein said piston spinning means comprise an axial flow turbine including:
    a plurality of circumferentially spaced apart vanes extending radially inwardly in part into said piston bore for engaging said fluid to cyclically rotate said piston upon aft travel of said piston toward said housing inlet.

6. A pump according to claim 5 wherein said second valve is disposed in said piston inlet.

7. A pump according to claim 3 wherein said piston spinning means comprise an integral rotary motor including:
    a pair of axially spaced apart stator bands each having a plurality of circumferentially adjoining spin coils disposed inside said housing and radially aligned with respective ones of said drive coils; and
    wherein said magnet rings have circumferentially spaced apart zones of different magnet field flux density and are positioned radially below respective ones of said stator bands for being magnetically rotated thereby.

8. A pump according to claim 7 wherein:
    said drive coils are disposed in symmetrical sets at opposite ends of said housing; and
    each of said stator bands is disposed axially coextensively with a respective one of said symmetrical sets, and radially inwardly thereof for simultaneously axially translating and rotating said piston in said housing.

9. A pump according to claim 8 wherein said drive coils include layers of coil windings, with adjacent layers having opposite helix angles.

10. A pump according to claim 3 further comprising means for commutating electrical current into respective ones of said drive coils for magnetically translating said piston in an axial forward stroke from said housing inlet toward said housing outlet, and in turn in an axial aft stroke from said housing outlet toward said housing inlet for oscillating said piston in said housing to cyclically pump said fluid axially therethrough.

11. A pump according to claim 10 wherein said commutating means comprise an electrical controller operatively joined to said drive coils for sequentially supplying electrical current thereto for axially oscillating said piston.

12. A pump according to claim 11 wherein said drive coils and magnet rings have equal axial individual lengths so that stroke of said piston is an integer multiple of said magnet ring length.

13. A pump according to claim 11 wherein said commutating means are effective for supplying said electrical current to said drive coils proportional to an amount of overlap of said drive coils with said magnet rings.

14. A pump according to claim 13 wherein:
    said commutating means further comprise a position sensor mounted in said housing adjacent to said piston for determining axial position of said piston; and
    said position sensor is operatively joined to said controller for providing position of said piston thereto for commutating said drive coils.

15. A pump according to claim 14 wherein said position sensor comprises:
    a magneto resistor and cooperating position magnet mounted in said housing adjacent to said piston;
    a position sleeve mounted coaxially in said piston adjacent to said housing bore, and including a plurality of circumferentially extending position poles defined between a respective plurality of annular grooves;
    said magneto resistor and position sleeve being mounted adjacent to each other for defining a magnetic circuit therebetween; and
    said magneto resistor being operatively joined to said controller for counting said position poles upon axial travel of said piston for sensing position thereof.

16. A pump according to claim 15 further comprising a second one of said position sensors operatively joined to said controller, and cooperating magnetically with a common position sleeve, and displaced 90 electrical degrees from said first position sensor for determining axial direction of piston movement in forward and aft strokes.

17. A pump according to claim 11 wherein said controller comprises means for monitoring electrical current to said drive coils for determining differential pressure across said piston.

18. A pump according to claim 11 wherein said controller comprises means for controlling axial position and velocity in said piston.

19. A pump according to claim 18 wherein said controller further comprises means operatively joined to said piston spinning means for controlling spin thereof.

20. A pump according to claim 3 further comprising means disposed at said journal bearing gap for pumping a portion of said fluid from said housing bore into said gap for accommodating leakage from said gap at opposite ends of said piston.

21. A pump according to claim 20 wherein said bearing pumping means comprise a screw pump including a plurality of circumferentially spaced apart screw threads having respective screw grooves therebetween for channeling said fluid therethrough.

22. A pump according to claim 21 wherein said screw pump further comprises an annular manifold disposed in flow communication with said screw grooves for collecting said fluid therefrom to uniformly distribute said fluid circumferentially around said bearing gap.

23. A pump according to claim 22 wherein said screw pump is disposed adjacent to said piston outlet.

24. A pump according to claim 22 wherein said screw pump is disposed in said piston journal at one axial end of said piston.

25. A pump according to claim 22 wherein said screw threads are defined by sidewalls extending radially inwardly from said journal to respective groove bottoms, and said sidewalls are tapered axially adjacent to said journal for minimizing flow separation of said fluid as it flows into and out of said screw grooves.

26. A pump according to claim 25 wherein said sidewall taper is less than about 10°.

27. A pump according to claim 22 wherein said screw pump includes only four of said screw threads and grooves equiangularly circumferentially spaced apart from each other, with each having a screw inlet disposed at an end of said piston for receiving said fluid thereat.

28. A pump according to claim 3 wherein said housing and piston are encapsulated in a biocompatible material for being implanted into a living body for pumping blood as said fluid through said housing and piston bores.

29. A pump for pumping a fluid comprising:
a housing having a bore disposed in flow communication between a housing inlet and a housing outlet spaced apart at opposite ends of said housing, and a first check valve fixedly joined thereto for controlling flow of said fluid through said housing bore;
a piston disposed coaxially in said housing bore for axial translation therein, and having a coaxial bore disposed in flow communication between a piston inlet and a piston outlet axially spaced apart at opposite ends of said piston, and a second check valve fixedly jointed thereto for controlling flow of said fluid through said piston bore;
said piston further including a radially outer surface spaced radially inwardly from said housing bore to define a radial gap therebetween being axially coextensive with said piston bore between said piston inlet and outlet for channeling a portion of said fluid axially therethrough; and
means for axially oscillating said piston in said housing for cyclically pumping said fluid in turn through said housing and piston inlets and outlets in unidirectional flow through said housing and piston bores.

30. A pump according to claim 29 further comprising means for suspending said piston inside said housing bore during said piston oscillation to provide only fluid contact therebetween.

31. A pump according to claim 30 wherein said suspending means are effective for hydrodynamically supporting said oscillatory piston in said housing using said fluid as bearing fluid in said gap.

32. A pump according to claim 31 wherein said suspending means comprise a linear hydrodynamic bearing defined between said piston outer surface and said housing bore.

33. A pump according to claim 31 wherein said suspending means comprise a rotary hydrodynamic journal bearing defined between said piston outer surface and said housing bore.

34. A pump according to claim 33 further comprising means for spinning said piston for circumferentially developing hydrodynamic pressure in said bearing fluid.

35. A pump according to claim 34 wherein said piston spinning means comprise a rotary motor including:
an annular rotor magnet having a plurality of circumferentially adjoining rotor poles; and
a stator band having a plurality of circumferentially adjoining spin coils disposed in said housing for magnetically cooperating with said rotor magnet for rotating said piston.

36. A pump according to claim 34 wherein said piston spinning means comprise an axial flow turbine including:
a plurality of circumferentially spaced apart vanes extending radially inwardly in part into said piston bore for engaging said fluid to cyclically rotate said piston upon aft travel of said piston toward said housing inlet.

37. A pump according to claim 36 wherein said second valve is disposed in said piston inlet.

38. A pump according to claim 31 wherein said piston oscillating means comprise a linear motor including a plurality of axially aligned drive coils disposed in said housing, and a magnet disposed in said piston and spaced radially inwardly of said drive coils for magnetically cooperating therewith to axially oscillate said piston in said housing for pumping said fluid through said housing and piston bores.

39. A pump according to claim 38 further comprising means for spinning said piston for circumferentially developing hydrodynamic pressure in said bearing fluid to define a rotary journal bearing between said piston outer surface and said housing bore.

40. A pump according to claim 39 wherein:
said piston further includes a pair of said magnets axially spaced apart in respective rings; and
said piston spinning means comprise an integral rotary motor including:
a pair of axially spaced apart stator bands each having a plurality of circumferentially adjoining spin coils disposed inside said housing and radially aligned with respective ones of said drive coils; and
wherein said magnet rings have circumferentially spaced apart zones of different magnet field flux density and are positioned radially below respective ones of said stator bands for being magnetically rotated thereby.

41. A pump according to claim 40 wherein:
said drive coils are disposed in symmetrical sets at opposite ends of said housing; and
each of said stator bands is disposed axially coextensively with a respective one of said symmetrical sets, and radially inwardly thereof for simultaneously axially translating and rotating said piston in said housing.

42. A pump according to claim 41 wherein said drive coils include layers of coil windings, with adjacent layers having opposite helix angles.

43. A pump according to claim 29 further comprising means for commutating electrical current into respective ones of said drive coils for magnetically translating said piston in an axial forward stroke from said housing inlet toward said housing outlet, and in turn in an axial aft stroke from said housing outlet toward said housing inlet for oscillating said piston in said housing to cyclically pump said fluid axially therethrough.

44. A pump according to claim 43 wherein said commutating means comprise an electrical controller operatively joined to said drive coils for sequentially supplying electrical current thereto for axially oscillating said piston.

45. A pump according to claim 44 wherein:

said piston oscillating means comprise a linear motor including a plurality of axially adjoining drive coils disposed in said housing, and a pair of axially spaced apart magnet rings disposed in said piston and spaced radially inwardly of said drive coils for magnetically cooperating therewith to axially oscillate said piston in said housing for pumping said fluid in turn through said housing and piston inlets and outlets in unidirectional flow through said housing and piston bores; and said drive coils and magnet rings have equal axial individual lengths so that stroke of said piston is an integer multiple of said magnet ring length.

46. A pump according to claim 44 wherein said commutating means are effective for supplying said electrical current to said drive coils proportional to an amount of overlap of said drive coils with said magnet rings.

47. A pump according to claim 46 wherein:

said commutating means further comprise a position sensor mounted in said housing adjacent to said piston for determining axial position of said piston; and said position sensor is operatively joined to said controller for providing position of said piston thereto for commutating said drive coils.

48. A pump according to claim 47 wherein said position sensor comprises:

a magneto resistor and cooperating position magnet mounted in said housing adjacent to said piston;

a position sleeve mounted coaxially in said piston adjacent to said housing bore, and including a plurality of circumferentially extending position poles defined between a respective plurality of annular grooves;

said magneto resistor and position sleeve being mounted adjacent to each other for defining a magnetic circuit therebetween; and said magneto resistor being operatively joined to said controller for counting said position poles upon axial travel of said piston for sensing position thereof.

49. A pump according to claim 48 further comprising a second one of said position sensors operatively joined to said controller, and cooperating magnetically with a common position sleeve, and displaced 90 electrical degrees from said first position sensor for determining axial direction of piston movement in forward and aft strokes.

50. A pump according to claim 44 wherein said controller comprises means for monitoring electrical current to said drive coils for determining differential pressure across said piston.

51. A pump according to claim 44 wherein said controller comprises means for controlling axial position and velocity in said piston.

52. A pump according to claim 51 wherein said controller further comprises means operatively joined to said piston spinning means for controlling spin thereof.

53. A pump according to claim 29 wherein said piston includes a cylindrical journal spaced radially inwardly of said housing bore to define a rotary hydrodynamic journal bearing therewith for channeling said fluid.

54. A pump according to claim 53 further comprising means disposed at said gap for pumping a portion of said fluid from said housing bore into said gap for accommodating leakage from said gap at opposite ends of said piston.

55. A pump according to claim 54 wherein said bearing pumping means comprise a screw pump including a plurality of circumferentially spaced apart screw threads having respective screw grooves therebetween for channeling said fluid therethrough.

56. A pump according to claim 55 wherein said screw pump further comprises an annular manifold disposed in flow communication with said screw grooves for collecting said fluid therefrom to uniformly distribute said fluid circumferentially around said bearing gap.

57. A pump according to claim 56 wherein said screw pump is disposed adjacent to said piston outlet.

58. A pump according to claim 56 wherein said screw pump is disposed in said piston journal at one axial end of said piston.

59. A pump according to claim 56 wherein said screw threads are defined by sidewalls extending radially inwardly from said journal to respective groove bottoms, and said sidewalls are tapered axially adjacent to said journal for minimizing flow separation of said fluid as it flows into and out of said screw grooves.

60. A pump according to claim 59 wherein said sidewall taper is less than about 10°.

61. A pump according to claim 56 wherein said screw pump includes only four of said screw threads and grooves equiangularly circumferentially spaced apart from each other, with each having a screw inlet disposed at an end of said piston for receiving said fluid thereat.

62. A pump according to claim 29 wherein said housing and piston are encapsulated in a biocompatible material for being implanted into a living body for pumping blood as said fluid through said housing and piston bores.

* * * * *